United States Patent
Ho et al.

(10) Patent No.: US 9,416,429 B2
(45) Date of Patent: Aug. 16, 2016

(54) APPARATUS AND METHODS FOR MANIPULATION AND OPTIMIZATION OF BIOLOGICAL SYSTEMS

(71) Applicant: THE REGENTS OF THE UNIVERSITY OF CALIFORNIA, Oakland, CA (US)

(72) Inventors: Chih-Ming Ho, Brentwood, CA (US); Pak Kin Wong, Tuscon, AZ (US); Ren Sun, Pacific Palisades, CA (US); Fuqu Yu, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/281,664

(22) Filed: May 19, 2014

(65) Prior Publication Data

US 2014/0363805 A1 Dec. 11, 2014

Related U.S. Application Data

(60) Continuation of application No. 13/562,216, filed on Jul. 30, 2012, now Pat. No. 8,765,459, which is a division of application No. 11/719,749, filed as application No. PCT/US2005/042096 on Nov. 18, 2005, now Pat. No. 8,232,095.

(60) Provisional application No. 60/629,500, filed on Nov. 18, 2004.

(51) Int. Cl.
*C12Q 3/00* (2006.01)
*G01N 35/00* (2006.01)
*C12Q 1/02* (2006.01)

(52) U.S. Cl.
CPC .. *C12Q 3/00* (2013.01); *C12Q 1/02* (2013.01); *G01N 35/0092* (2013.01); *G01N 2035/0094* (2013.01)

(58) Field of Classification Search
CPC ........ C12Q 3/00; C12Q 1/02; G01N 35/0092; G01N 2035/0094
USPC ...................................................... 435/289.1
See application file for complete search history.

(56) References Cited

U.S. PATENT DOCUMENTS

| | | |
|---|---|---|
| 5,081,035 A | 1/1992 | Halberstadt et al. |
| 6,009,379 A | 12/1999 | Kurtzberg et al. |

(Continued)

FOREIGN PATENT DOCUMENTS

| | | |
|---|---|---|
| WO | WO-99/58479 | 11/1999 |
| WO | WO-03/087292 | 10/2003 |

OTHER PUBLICATIONS

Buchholz et al,. Metabolomics: quantification of intracellular metabolite dynamics, Elsevier Science B.V. (2002) 19:5-15.

(Continued)

*Primary Examiner* — Lore Jarrett
(74) *Attorney, Agent, or Firm* — Foley & Lardner LLP; Cliff Z. Liu; Angela D. Murch

(57) ABSTRACT

A method for optimization of a response of a biological system includes: (1) obtaining measurements of a biological system in response to varying concentrations of drugs in a drug combination; (2) fitting the measurements into a model of the biological system; and (3) using the model of the biological system, predicting concentrations of the drugs in the drug combination to yield an optimized response of the biological system.

6 Claims, 9 Drawing Sheets

(56) References Cited

U.S. PATENT DOCUMENTS

| | | | |
|---|---|---|---|
| 6,073,482 | A | 6/2000 | Moles |
| 6,114,164 | A | 9/2000 | Dennis et al. |
| 6,395,538 | B1 | 5/2002 | Naughton et al. |
| 6,651,046 | B1 | 11/2003 | Sato et al. |
| 6,882,992 | B1 | 4/2005 | Werbos |
| 2002/0037499 | A1 | 3/2002 | Quake et al. |
| 2002/0146817 | A1* | 10/2002 | Cannon et al. ............ 435/289.1 |
| 2003/0123051 | A1 | 7/2003 | McGrew |
| 2005/0153436 | A1 | 7/2005 | Vilendrer |
| 2005/0186671 | A1 | 8/2005 | Cannon et al. |

OTHER PUBLICATIONS

Cohen, Science (1993) 260:1258.
Forrest, Science (1993) 261:872-878.
Fung et al., Nature (2005) 435:118-122.
Golub, Nature Medicine (2003) 9(5):510-511.
Gu et al., PNAS USA (2004) 101(45):15861-15866.
Ho et al., Progress in Aerospace Sciences (2003) 39:635-681.
International Search Report and Written Opinion for PCT/US05/42096, mailed Jul. 3, 2008, 7 pages.
Sarkar et al., Optimisation of fed-bath bioreactors using genetic algorithms, Elsevier Science LTD. (2003) 58:2283-2296.
Stancovski and Baltimore, Cell (1997) 91:299-302.
Tung and Kleinrock, IEEE Transactions on Parallel and Distributed Systems (1996) 7(4):439-448.
US Notice of Allowance on U.S. Appl. No. 11/719,749 dated Mar. 20, 2012.
US Notice of Allowance on U.S. Appl. No. 13/562,216 dated Feb. 20, 2014.
US Office Action on U.S. Appl. No. 11/719,749 dated Jan. 10, 2012.
US Office Action on U.S. Appl. No. 11/719,749 dated Nov. 9, 2010.
US Office Action on U.S. Appl. No. 11/719,749 dated Apr. 14, 2011.
US Office Action on U.S. Appl. No. 13/562,216 dated Dec. 12, 2013.
US Office Action on U.S. Appl. No. 13/562,216 dated May 3, 2013.
Wong et al., Journal of Microelectromechanical Systems (2004) 13(6):940-946.

* cited by examiner

APPARATUS AND METHODS FOR MANIPULATION AND OPTIMIZATION OF BIOLOGICAL SYSTEMS

RELATED APPLICATIONS

This application is a continuation of U.S. application Ser. No. 13/562,216, filed Jul. 30, 2012, which is a divisional application of U.S. application Ser. No. 11/719,749, filed Aug. 4, 2008, now issued as U.S. Pat. No. 8,232,095, which is the national phase of PCT Application No. PCT/US2005/042096, filed on Nov. 18, 2005 which claims the benefit of priority of U.S. provisional application Ser. No. 60/629,500 filed Nov. 18, 2004, and all of which are expressly incorporated herein by reference in their entirety and for all purposes.

STATEMENT OF RIGHTS TO INVENTIONS MADE UNDER FEDERALLY SPONSORED RESEARCH

This invention was made with Government support under NCC2-1364 awarded by the National Aeronautics and Space Administration. The Government has certain rights in the invention.

TECHNICAL FIELD

The invention provides apparatus and methods for conducting automatic analysis and manipulation, e.g., experiments and systems optimization, on biological samples, e.g., viable biological samples, including, but not limited to cells, tissues, organs cultures and the like, e.g., plant and mammalian cells, a cell culture, cell fragments and/or cell organelles, a tissue, an isolated organ, a microorganism, e.g., bacteria, protozoa, yeast and viruses.

In alternative aspects, systems include a device for sustaining cells or tissue samples, one or more actuators for stimulating the samples via biochemical, electromagnetic, thermal, mechanical, and/or optical stimulation, one or more sensors for measuring a biological response signal of the samples resulting from the stimulation of the sample. In one aspect, the systems and methods of the invention use at least one optimization algorithm to modify the actuator's control inputs for stimulation, responsive to the sensor's output of response signals. The compositions and methods of the invention can be used, e.g., for, but not limited to, the following applications: systems optimization of any biological manufacturing or experimental system, e.g., bioreactors for proteins, polypeptides or peptides for vaccines, and the like, directing differentiation of cells to a specific property, e.g., therapeutic proteins, polypeptides or peptides for vaccines, and the like, and determining specific combination of ligands and their corresponding concentrations in drug screening systems, small molecules (e.g., antibiotics), polysaccharides, lipids, and the like.

BACKGROUND

Sophisticated biological systems, as often occur in nature, such as cells, tissues, and organs in the human body for example, are capable of responding to external chemical and/or physical stimuli ("input variables" in some systems parlance). Such stimuli can additionally be applied as spatial or temporal gradients. The responses of biological systems can nonlinearly depend on the stimuli in a complex interplay of multiple variables comprising external stimuli from the environment and internal factors within the biological system. This interplay can involve synergistic and antagonistic relationship among the multiple input variables.

As a result of such complexity, It can be difficult to manipulate a biological system, such as a cell, a group of cells, and organ or tissue, to behave in a desirable or nearly optimal way without understanding the following: (i) the effects that each input variable (e.g., type of control input) has on a system, (ii) the different possible states of each variable (specific parameter of the control input), (iii) how those states affect the overall system, and (i v) the effects of interactions among the variables. The inability to manipulate a complex biological system posts challenges to elucidating mechanisms of cellular processes although such information can contribute significantly to the advancement of basic research and medical applications. Further, cellular processes can be dynamic, stochastic, nonlinear, multi-parametric, and/or possess memory effects. An example is cells which regulate their activities by integrating multiple external stimuli using internal and external cellular signal transduction networks. A signal transduction network is a cascade of biochemical reactions in the cells that can modify the cellular activity, such as a transcription factor activity in response to the binding of an external stimulus such as a ligand that binds to a corresponding receptor.

In a biological experiment for understanding the above-described signal transduction pathway, each stimulus, for example a ligand such as a drug or a cytokine, or other changes in the physical or chemical environment, can be tested independently, via an independent variation approach. Elements in signal transduction pathways that responds to a stimulus can be identified in an effort to reconstruct the signal transduction pathway and associated biological responses from downstream cellular processes. Due to the complexity of biological systems, the transduction pathway identification and reconstruction process can be extremely time-consuming and typically provides only partial information on the pathway. Furthermore, interactions between or among stimuli can be missed by such an independent variation approach. Therefore, important information in the combinatorial control, which can occur naturally in biological systems, is unavailable.

In combinatorial control, the combinations of the inputs can interact nonlinearly, in an antagonistic and/or a synergistic fashion. Instead of one to one correspondence of the input and output relationships, specific combinations can result in different responses. For example, it is estimated that only about 160 transcription factors exist in the yeast genome, but yeast cells contain thousands of co-regulated sets of genes: Further, it is difficult to determine combinations of control inputs, such as a specific ligands and specific concentrations of the ligands, for eliciting a desired response from a biological sample representing a biological system. Examples of other biological experiments that illustrate problems associated with the determination of combinatorial control include specific combinations of drugs and their corresponding concentrations in combination drug treatment, or in identifying the proper combination of environment cues in nature for a specific biological response.

One approach is to test all the combinations of the different stimuli (e.g.; different ligands, or chemical or physical conditions) and the different states of each stimulus (e.g., different concentrations of a specific ligand, or different values of pH, temperature, shear stress, electrical field, magnetic field, etc.). However, the number of tests (experiments) required increases exponentially with the number of different stimuli (or "input variables" or "control inputs" in some systems terminology). The number of tests can become impracticably large in terms of cost and time for large numbers of input variables. For example, testing the effectiveness of a six-drug combination cocktail on a tissue or cell sample, assuming only ten different concentrations per drug is used, requires $10^6$ or one million tests in order to identify a nearly optimal blend of concentrations. The identification of substantially optimal stimulus conditions for a desired biological response with a more limited number of tests is very desirable.

For decades, flu vaccines have been manufactured growing viruses in millions of live, fertilized eggs. The system works well, but it is time consuming and hard to ramp up quickly in a public health emergency. The threat of a flu pandemic demands new methods for developing newer, faster production systems for vaccines, including vaccines for flu, SARS and the like. Cell-based production methods grow the flu virus in steel vats filled with living cells derived from monkeys, dogs, humans or even insects. Some vaccines produced this way have won limited approval in Europe, but none has been cleared for use in the United States.

SUMMARY

The invention provides systems and methods manipulating, controlling, optimizing biological systems, e.g., for eliciting a more desired biological response of biological sample, such as a tissue, organ, and/or a cell. In one aspect, systems and methods of the invention operate by monitoring stimuli and conditions in a biosystem, including parameters or representative biological samples sustained in the system. In alternative aspects, systems of the invention include a device for sustaining cells or tissue samples, one or more actuators for stimulating the samples via biochemical, electromagnetic, thermal, mechanical, and/or optical stimulation, one or more sensors for measuring a biological response signal from or condition in a sample resulting from the growth and/or stimulation of the sample. In one aspect, the systems and methods of the invention comprise at least one algorithm, e.g., an optimization algorithm such as a smart non-linear optimization search algorithm, e.g., in the context of an interactive software and hardware system, e.g., as a computer implemented method.

The algorithm, e.g., optimization algorithm, can be used to monitor and/or control any or all aspects of a system, e.g., a biosystem, including environmental parameters, system inputs and system outputs. In one aspect, a smart non-linear optimization search algorithm is used to monitor stimuli and conditions in a biosystem, e.g., to modify the actuator's control inputs for stimulation responsive to a sensor's output of response signals. Smart non-linear optimization search algorithms used in the systems and methods of the invention can comprise, e.g., a simulated annealing algorithm, a stochastic local search algorithm, a stochastic hill-climbing algorithm, a Metropolis-Hastings sampler algorithm, a greedy randomized adaptive search algorithm, an evolutionary algorithm, a genetic algorithm, a taboo search algorithm, and/or a Gur Game algorithm, or any combination thereof.

The compositions and methods of the invention can be used, e.g., for, but not limited to, the following applications: systems manipulation and/or optimization of any biological manufacturing or experimental system, e.g., bioreactors for proteins, polypeptides or peptides for vaccines, and the like, directing differentiation of cells to a specific property, and determining specific combination of ligands and their corresponding concentrations in drug screening systems. The compositions and methods of the invention can be used, e.g., to for systems optimization of any biological manufacturing or experimental system, e.g., bioreactors for proteins, e.g., therapeutic proteins, polypeptides or peptides for vaccines, and the like, small molecules (e.g., antibiotics), polysaccharides, lipids, and the like.

Some embodiments of the current invention provide systems and methods to automatically, interactively, and/or experimentally determine optimal control in puts (values of variables) for eliciting a desired biological system response, e.g., cell differentiation, drug cocktail, and determining specific combination of ligands and their corresponding concentrations in drug screening system. These embodiments can provide a way to determine the variables, the (e.g., types of control in put) that are important for a desired system response, and states of each important variable (specific parameter of the control input) that elicit a substantially optimal biological system response. These embodiments can obviate the need to run a large number of tests, thereby dramatically reducing the time and resources required to identify input variables and corresponding values to elicit an optimized, e.g., a substantially optimum (or nearly optimized— i.e., minimal optimization is sufficient) biological system response.

In one embodiment, a system of the invention comprises: (i) a cell, organ or tissue culture device, a bioreactor, an artificial organ system, including similar devices or systems, for sustaining biological samples representative of (e.g., derived from) the biological system to be studied or manipulated, as in a manufacturing biosystem; (ii) one or more actuators for stimulating the samples, e.g., via chemical, electromagnetic, thermal, mechanical, optical, and/or other environmental stimulation; (iii) one or more sensors for measuring the response signal of the samples resulting from the stimulation; and (iv) a controller executing a smart search algorithm to modify the actuator's control inputs for subsequent biological sample manipulation and/or stimulation responsive to the sensors' outputs responsive to biological sample responses.

Embodiments can also comprise appropriate software and hardware components to provide user-interface and data analysis capabilities to enable user monitor and control of the automatic optimization process. Thus, the invention comprises computer program products for implementing system optimization comprising smart non-linear optimization search algorithms, e.g., a simulated annealing algorithm, a stochastic local search algorithm, a stochastic hill-climbing algorithm, a Metropolis-Hastings sampler algorithm, a greedy randomized adaptive search algorithm, an evolutionary algorithm, a genetic algorithm, a taboo search algorithm, and/or a Gur Game algorithm, or any combination thereof. The invention also provides computer implemented methods comprising these algorithms for automatic optimization processes, including for the monitoring and/or control of experimental and manufacturing biosystems.

Embodiments can utilize biological system response information obtained from the measurements by the sensors. Based partly on such information, in some embodiments a stochastic search algorithm (e.g., a smart non-linear optimization search algorithm, such as a Gur Game search algorithm) can iteratively determine the input variables for achieving a desired biological system, response. Cells or tissue samples can be sustained in a device that can maintain desired physical and chemical states of the biological samples for a predetermined (e.g., extended) period of time. Actuators, including biochemical and physical, can be provided to generate temporal and/or spatial stimulation. The states and responses of the samples can be monitored with instruments and/or sensors. In one aspect, a controller implementing an algorithm, e.g., an optimization algorithm such as a stochastic search algorithm, is used to automatically and iteratively modify the initial inputs in search of a more nearly optimal biological system response, e.g., output from a bioreactor, e.g., a microfluidic cell culture.

Four exemplary applications of embodiments of this invention comprise compositions and methods for the analysis, manipulation and/or optimization of: (i) systems for the manufacturing of polypeptides (e.g., antibodies or cytokines), small proteins (e.g., antigens for vaccines), small molecules (e.g., antibiotics, co-factors or vitamins), lipids, nucleic acids, sugars and polysaccharides, and other molecules; (ii) systems for directed cell differentiation and/or proliferation, such as in tissue engineering; (iii) systems for combination drug discovery or drug validation, e.g., using cocktails of candidate drugs; and (iv) systems for discovery in cell biology.

The invention provides systems for automatic manipulation of a biological sample (any biological material, such as a tissue, a cell, a virus, a plasmid and the like), comprising:

(a) a product of manufacture operable to sustain a biological sample positioned therein; (b) at least one stimulator operable to alter at least one parameter to which the biological sample is exposed; (c) at least one sensor operable to measure the at least one parameter; and (d) a controller operably connected to receive a signal from the at least one sensor such that the controller is responsive to the signal received from the sensor to actuate the at least one stimulator to which it is operably connected, and the stimulator upon actuation provides a stimulus to alter the at least one parameter measured in step (c), or at least one other parameter, or a combination thereof, within or affecting the product of manufacture, thereby manipulating the biological sample, wherein the controller comprises or is operably connected to an algorithm to automatically determine the stimulus given to the biological sample, and the determination is based at least in part on the at least one parameter measured by the sensor in step (c).

In one aspect, the algorithm is an optimization algorithm or a manipulation algorithm. The controller can comprise or is operably connected to a computer program product comprising the algorithm to automatically determine the stimulus given to the biological sample. The computer program product can be operably contained within (e.g., programmed into) a microchip, a microprocessor, a computer or a combination thereof. In one aspect, the controller comprises or is operably connected to an analog neural network, a hot wire circuitry, a microprocessor, a computer or a combination thereof, comprising the algorithm to automatically determine the stimulus given to the biological sample. In one aspect, the optimization algorithm comprises computer program product as set forth in FIG. 6; or, the optimization algorithm has a logic flow as set forth in FIG. 6.

In one aspect, the biological sample comprises a cell, a cell culture, a tissue, an isolated organ or an organ system or a cell isolate. The cell can be a bacterial cell, a protozoan cell, an insect cell, a yeast cell, a plant cell or a mammalian cell, wherein optionally the mammalian cell is a human cell. In one aspect, the product of manufacture comprises a bioreactor, e.g., a composition comprising a cell culture apparatus.

In one aspect, at least one parameter altered by the at least one stimulator comprises an environmental condition in the product of manufacture. The environmental condition can be altered by the at least one stimulator in the product of manufacture comprises temperature, pH, oxygen or carbon dioxide concentration, nutrient or waste concentration, rate of exchange of cell or tissue culture nutrients, rate of harvesting or removal of a cell or tissue culture secreted product, cell growth or differentiation rate, cell concentration, or a combination thereof.

In one aspect, the stimulus applied in step (d) for altering the at least one parameter measured in step (c), or at least one other parameter, or a combination thereof, within the product of manufacture, or affecting the product of manufacture, comprises a biochemical, electromagnetic, thermal, mechanical and/or optical stimulation. In one aspect, the stimulus applied in step (d) for altering the at least one parameter measured in step (c), or at least one other parameter, or a combination thereof, within the product of manufacture comprises a change in temperature, pH, oxygen or carbon dioxide concentration, rate of exchange of cell or tissue culture nutrients, rate of harvesting or removal of a cell or tissue culture secreted product, or a combination thereof.

In one aspect, the algorithm is operably linked to the controller, the sensor and/or the stimulator, or any other apparatus or system to which the system of the invention is also linked with or communicating with. In one aspect, more than one algorithm is used, e.g., in parallel or multiplex linked systems, e.g., for communicating with another apparatus or system to which the system of the invention is also linked with or communicating with.

In one aspect, the algorithm manipulates one or more parameters in the system to achieve a desired result from the biological sample or the system. The algorithm can comprise an optimization algorithm to manipulate one or more parameters in the system to achieve an optimized desired result from the biological sample or the system. In alternative aspects, the term "optimized" includes "nearly optimized"—i.e., only minimal optimization. In other words, an optimization by a system or method of the invention can include partial, or minimal, optimization, in addition to being capable, in some aspects, complete optimization.

In one aspect, the desired result comprises growing, sustaining and/or differentiating the biological sample in the product of manufacture. The algorithm can manipulate or optimize a quantitative aspect (the amount of) and/or a qualitative aspect (the nature of) of the stimulus used to modify the one or more parameters in the system to achieve the desired result from the biological sample. In one aspect, the desired result from the biological sample generated by the algorithm's manipulation of the system comprises manipulation or optimization of: cell growth, cell differentiation, cell vitality, synthesis or secretion of a naturally occurring or recombinant protein, a small molecule, an antibiotic, a polysaccharide, a virus, a nucleic acid and/or a lipid. The naturally occurring or recombinant protein whose synthesis or secretion is manipulated or optimized can comprise a cytokine, an antibody, an antigen or a structural protein.

In one aspect, the algorithm is set to direct an iterative repetition of measuring at least one parameter in the system, actuating at least one stimulator and measuring at least one parameter modified in response to the stimulation, thereby manipulating and/or optimizing the biological system to achieve the desired result. The algorithm can be set to direct a dynamic change in the time period of each iteration. In one aspect, the algorithm is set to self-organize and/or self-optimize the automatic manipulation of the biological sample.

In one aspect, the algorithm comprises a smart non-linear optimization search algorithm, such as a simulated annealing algorithm, a stochastic local search algorithm, a stochastic hill-climbing algorithm, a Metropolis-Hastings sampler algorithm, a greedy randomized adaptive search algorithm, an evolutionary algorithm, a genetic algorithm, a taboo search algorithm, and/or a Gur Game algorithm, or any combination thereof, or variations thereof. The smart non-linear optimization search algorithm can be set as a biased random walk toward the desired result, and the desired result is set as a global optimum of a plurality of parameters. The algorithm can set a global figure of merit (a reward function) to measure the performance of the system as a whole to reach the desired result. In one aspect, the algorithm can assign each measured parameter any one of a pre-defined set of discrete states (or an automaton), and different inputs for each parameter, or different inputs for the same parameter over time, result in a different number of states and state values being assigned to each parameter, and during manipulation or optimization or the biological system each automaton moves from one state to another based on being rewarded for causing a desired response, and the reward probabilistically drives the system to the desired result.

The invention provides methods for automatic manipulation or optimization of a biological sample comprising (a) providing at least one system of the invention; (b) measuring at least one parameter in the biological sample, wherein the controller receives a signal from the at least one sensor; and (c) providing a stimulus to the biological sample to alter the at least one parameter measured in step (b), or at least one other parameter, or a combination thereof, within the product of manufacture by running the algorithm, wherein the algorithm determines the stimulus given to the biological sample, and the determination is based at least in part on the at least one parameter measured by the sensor in step (b), thereby automatically manipulating or optimizing the biological sample. The invention also provides methods for automatic manipulation or optimization of a biological sample to achieve a desired result comprising (a) providing at least one system of the invention; (b) providing a first stimulus to the biological sample; (c) measuring at least one parameter in the biological sample in response to the first stimulus, wherein the parameter is measured by the controller receiving a signal from the at least one sensor; and (d) providing at least a second stimulus to the biological sample to alter the at least one parameter measured in step (b), or at least one other para meter, or a combination thereof, to achieve a desired result, wherein the nature and amount of the at least second stimulus is determined and provided by running the algorithm, and the determination is based at least in part on the at least one para meter measured by the sensor in step (c). In one aspect of any method of the invention, the steps of the method can be iteratively repeated until a desired result is achieved.

In one aspect, the system used in any method of the invention comprises sustaining or growing a biological sample within an apparatus for growing or sustaining or handling a biological material, e.g., in an apparatus such as a bioreactor. In one aspect, the biological sample comprises a cell, a cell culture, a tissue, an isolated organ or an organ system or a cell isolate.

In one aspect of any method of the invention, the cell is a bacterial cell, a protozoan cell, an insect cell, a yeast cell, a plant cell or a mammalian cell, wherein optionally the mammalian cell is a human cell. In one aspect of any method of the invention, the product of manufacture comprises a bioreactor. The at least one parameter can be altered by the at least one stimulator, and the parameter can comprise an environmental condition in the product of manufacture or affecting the product of manufacture. In one aspect, the environmental condition altered by the at least one stimulator in the product of manufacture comprises temperature, pH, oxygen or carbon dioxide concentration, nutrient or waste concentration, rate of exchange of cell or tissue culture nutrients, rate of harvesting or removal of a cell or tissue culture secreted product, cell growth or differentiation rate, cell concentration, or a combination thereof. The stimulus applied in a step for altering the at least one parameter measured, or at least one other parameter, or a combination thereof, within the product of manufacture can comprise a biochemical, electromagnetic, thermal, mechanical and/or optical stimulation.

In one aspect of any method of the invention, the stimulus applied a step for altering the at least one parameter measured, or at least one other parameter, or a combination thereof, within the product of manufacture comprises a change in temperature, pH, oxygen or carbon dioxide concentration, rate of exchange of cell or tissue culture nutrients, rate of harvesting or removal of a cell or tissue culture secreted product, or a combination thereof.

In one aspect of any method of the invention, the algorithm manipulates one or more parameters in the system to achieve a desired result from the biological sample. The desired result can comprise growing, sustaining and/or differentiating the biological sample (e.g., cells, tissues) in the product of manufacture (e.g., a bioreactor).

In one aspect, the algorithm manipulates or optimizes a quantitative aspect (the amount of) and/or a qualitative aspect (the nature of) of the stimulus used to modify the one or more parameters in the system to achieve the desired result from the biological sample. The desired result from the biological sample generated by the algorithm's manipulation or optimization of the system can comprise manipulation or optimization of: cell growth, cell differentiation, cell vitality, synthesis or secretion of a naturally occurring or recombinant protein, a small molecule, an antibiotic, a polysaccharide, a virus, a nucleic acid and/or a lipid. In one aspect, the naturally occurring or recombinant protein whose synthesis or secretion is manipulated or optimized comprises a cytokine, an antibody or a structural protein.

In one aspect, the algorithm is set to direct an iterative repetition of measuring at least one parameter in the system, actuating at least one stimulator and measuring at least one parameter modified in response to the stimulation, thereby manipulating and/or optimizing the biological system to achieve the desired result. The algorithm can be set to direct a dynamic change in the time period of each iteration. In one aspect, the algorithm is set to self-organize and self-optimize the automatic manipulation of the biological sample. The algorithm can comprise a smart non-linear optimization search algorithm, such as a simulated annealing algorithm, a stochastic local search algorithm, a stochastic hill-climbing algorithm, a Metropolis-Hastings sampler algorithm, a greedy randomized adaptive search algorithm, an evolutionary algorithm, a genetic algorithm, a taboo search algorithm, and/or a Gur Game algorithm, or any combination thereof.

In one aspect, the smart non-linear optimization search algorithm is set as a biased random walk toward the desired result, and the desired result is set as a global optimum of a plurality of parameters. In one aspect, the algorithm sets a global figure of merit (a reward function) to measures the performance of the system as a whole to reach the desired result. The algorithm can assign each measured parameter any one of a pre-defined set of discrete states (or an automaton), and different in puts for each parameter, or different inputs for the same parameter over time, result in a different number of states and state values being assigned to each parameter, and during manipulation and/or optimization of the biological system each automaton moves from one state to another based on being rewarded for causing a desired response, and the reward probabilistically drives the system to the desired result.

The invention provides systems for automatically manipulating or optimizing production of a product by a biological system, comprising: (a) a bioreactor and a biological sample positioned therein; (b) at least one stimulator operable to alter at least one parameter to which the biological sample is exposed; (c) at least one sensor operable to measure the at least one parameter; and (d) a controller operably connected to receive a signal from the at least one sensor such that the controller is responsive to the signal received from the sensor to actuate the at least one stimulator, and the stimulator upon actuation provides a stimulus to alter the at least one parameter measured in step (c), or at least one other parameter, or a combination thereof, within the bioreactor, thereby manipulating the biological sample, wherein the controller comprises or is operably connected to a computer program product comprising an algorithm operably linked to the stimulator to automatically determine the stimulus given to the biological sample, and the determination is based at least in part on the at least one parameter measured by the sensor in step (c) and the rate or amount of product produced by a biological system, thereby automatically manipulating or optimizing production of the product by the biological system.

The invention provides computer-implemented methods for automatically optimizing production of a product by a biological system comprising a method of the invention. The invention provides computer program products for automatically optimizing production of a product by a biological system, wherein the computer program product comprises a machine-readable medium including machine-executable instructions, the instructions being operative to cause a machine to run a computer-implemented method of the invention. The invention provides computer systems comprising a computer program product of the invention.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto. The details of one or more embodiments of the invention are set forth in the accompanying drawings and the description below.

All publications, patents, patent applications, GenBank sequences and ATCC deposits, cited herein are hereby expressly incorporated by reference for all purposes.

DETAILED DESCRIPTION

Figure 1:
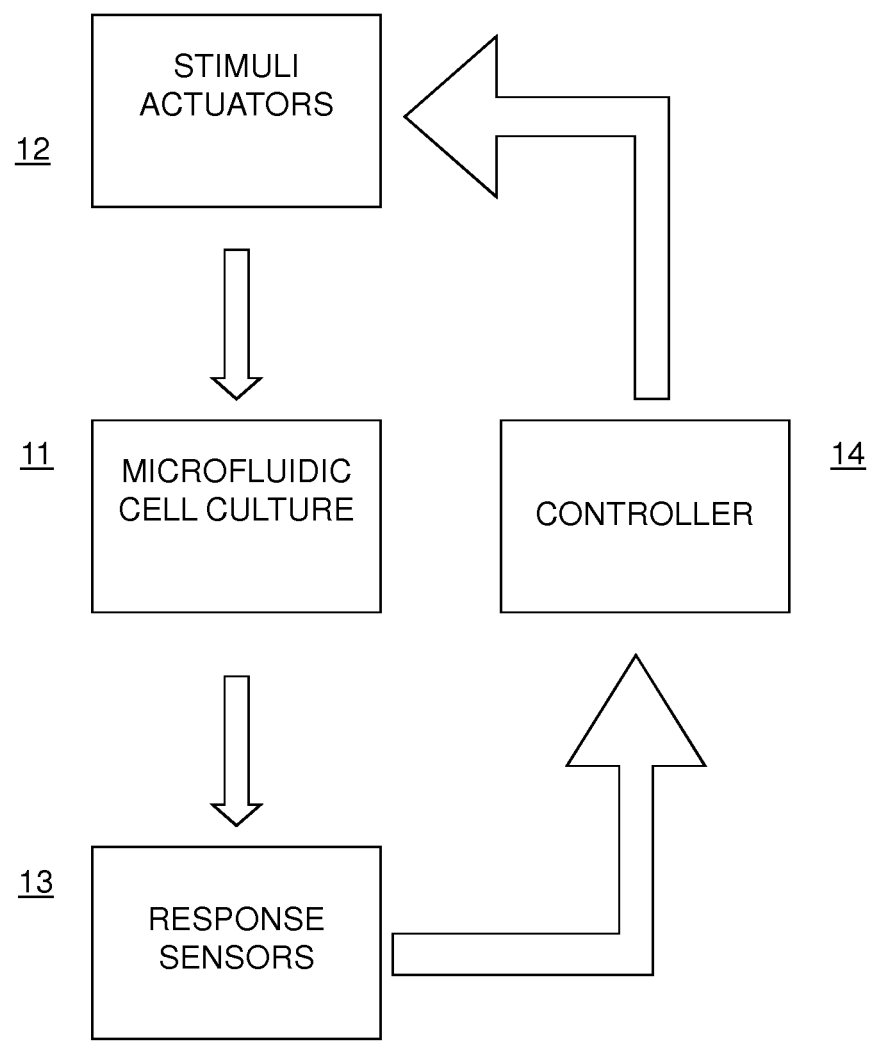
FIG. 1 is a high level block diagram of an exemplary embodiment of the invention.

The invention provides systems and methods for manipulating, e.g., optimizing and controlling, biological systems by using an optimization algorithm set for the automatic manipulation of the biological sample to elicit a desired response from the biological sample. The systems and methods of the invention can be used to manipulate, control, or optimize any biological system, including but not limited to, the following applications: systems optimization of a biological manufacturing or experimental system, e.g., bioreactors for proteins, polypeptides or peptides for vaccines, and the like, directing differentiation of cells to a specific property, and determining specific combination of ligands and their corresponding concentrations in drug screening systems. The invention provides apparatus and methods for conducting automatic analysis and manipulation, e.g., experiments and systems optimization, on biological samples, e.g., viable biological samples, including, but not limited to cells, tissues, organs cultures and the like, e.g., plant and mammalian cells, a cell culture, cell fragments and/or cell organelles, a tissue, an isolated organ, a microorganism, e.g., bacteria, protozoa, yeast and viruses. The invention provides apparatus and methods for conducting automatic analysis and manipulation and/or systems optimization on manufacturing systems for biological products, such as proteins (e.g., cytokines, vaccines), small molecules (e.g., antibiotics), lipids, polysaccharides, nucleic acids and the like. The invention provides apparatus and methods for conducting automatic analysis and manipulation and/or systems optimization in tissue engineering systems, such as systems for directed cell proliferation or differentiation. The invention provides apparatus and methods for conducting automatic analysis and manipulation and/or systems optimization in drug discovery systems, including cell-based drug discovery or drug efficacy verification systems, particularly in combination drug discovery or efficacy validation, e.g., using cocktails of candidate drug compounds. The invention provides apparatus and methods for conducting automatic analysis and manipulation and/or systems optimization in cell biology systems, including experimental systems, such as gene circuit, cell proliferation, programmed cell death (apoptosis) or signal transduction systems.

In one aspect, the systems and methods of the invention are used to optimize the production of biological products, including polypeptide and peptides, e.g., antibodies, antigens or cytokines (including recombinant proteins), small molecules made by cell-based or in vitro biological systems, lipids, polysaccharides, nucleic acids, viruses, recombinant vectors and the like. Thus, in one aspect, the systems and methods of the invention are used to optimize the production of vaccines and medicines. In another aspect, the systems and methods of the invention are used to direct differentiation of cells into a group of cells with specific properties such as having a specific surface marker. In another aspect, the systems and methods of the invention are used to identify the specific combination of ligands and their corresponding concentrations.

In the following description, reference is made to the accompanying drawings, which illustrate several embodiments of the present invention. It is understood that other embodiments may be utilized and mechanical, compositional, structural, electrical, and operational changes may be made without departing from the spirit and scope of the present disclosure. The following detailed description is not to be taken in a limiting sense, and the scope of the embodiments of the present invention is defined only by the claims of the issued patent.

Some portions of the detailed description which follows are presented in terms of procedures, steps, logic blocks, processing, and other symbolic representations of operations on data bits that can be performed on computer memory. In alternative aspects, the systems of the invention comprise a computer implemented method, a procedure, a computer executed step, a logic block, a process, etc., to be a self-consistent sequence of steps or instructions leading to a desired result, as described herein. In one aspect, the steps are those utilizing physical manipulations of physical quantities, e.g., parameters in a biological system. These quantities can take the form of electrical, magnetic, or radio signals capable of being stored, transferred, combined, compared, and otherwise manipulated by a computer system. In various aspects, these signals are referred to at times as bits, values, elements, symbols, characters, terms, numbers, or the like. Each step may be performed by hardware, software, firmware, human (operator) manipulation or any combinations thereof.

Embodiments of the present invention provide apparatus and methods to determine the variables or parameters (the different types of control inputs or stimuli) and the specific value of each of the variables or parameters (e.g., a specific metric of each input or stimulus) that singly or in combination can elicit a desirable and/or substantially optimal response from a biological system, such as a biological sample. In alternative aspects, the biological sample comprises a single cell, a cell or tissue culture, or a tissue sample, or an isolated organ, without requiring knowledge of the internal mechanisms of the biological system.

The systems and methods of the invention can obviate or reduce the need to run a large, e.g., an impracticably large, number of tests. Embodiments can comprise: (i) a device for sustaining cells, cell or tissue cultures, or tissue samples, or organs; (ii) one or more actuators for stimulating a biological sample, e.g., via chemical, electromagnetic, thermal, mechanical, optical, and/or other environmental stimulation, according to a selected criterion; (iii) one or more sensors for measuring the corresponding responses of the samples resulting from the stimulation; and (iv) a controller executing an optimization algorithm to modify the actuator's control in puts for subsequent stimulation responsive to the sensors' outputs responsive to biological sample responses. Embodiments can also include appropriate software and hardware components to provide user-interface and data analysis capabilities to a enable user to monitor and control the automatic experimentation process.

FIG. 1 illustrates a high level functional block diagram of an embodiment of the invention. In this embodiment, the exemplary device for sustaining cells, cell cultures, and tissue samples is a microfluidic cell culture device (a type of bioreactor) 11. This exemplary device can sustain the cells and tissue samples for extended periods of time. The length of time required depends on the biological process and transduction network under investigation, which can be up to months or even longer. The exemplary device can provide the basic elements for sustaining biological samples, such as growth factor, cytokine(s), extra-cellular matrix, temperature, pH, gases, and ions that are required for normal cell survival and processes. Some embodiments require ongoing monitoring and stimulation of biological samples under test. Embodiments of the sample-sustaining devices can allow integration of corresponding sensors and actuators.

Referring again to FIG. 1, block 12 represents stimuli actuation to stimulate a biological sample within the exemplary microfluidic cell culture (bioreactor) 11 under control of controller 14. Some stimuli actuators may be integrated with microfluidic cell culture 11: for example, electrodes, temperature actuators, and mechanical actuators (or, in alternative aspects, stimuli actuators may be integrated in any form of bioreactor). Other stimuli actuator can be separate from microfluidic cell culture 11: for example various media and reagent pumps or valves under control of controller 14. Block 13 represents sensing responses of the biological sample. In this exemplary embodiment or in any other aspect of the invention, response sensing can include, without limitation: sensing chemicals in cell culture media, sensing intracellular chemicals; sensing electrical fields and membrane potentials, and imaging of the biological sample using bright field, phase contrast, fluorescence, and/or atomic force microscopy. Block 14 represents the controlling function, which in some embodiments can be implemented using a personal computer executing software.

In this exemplary embodiment or in any other aspect of the invention, a device (e.g., a microfluidic cell culture device) can be fabricated, for example, by micromolding. In one aspect, the molding is polydimethylsiloxane (PDMS) (Sylgard 184) on a photoresist master mold to form fluid channels and/or other structures therein. Master molds for micromolding can be fabricated by photolithography of positive photoresist SJ R 5740 (MicroChem, 4100 I). Three layers of photoresist can be spun on a glass substrate to achieve a final thickness of 60 μm. After curing, a PDMS replica can be carefully peeled off a master mold. The channels and/or other structures can then be sealed with cover glasses of about 0.17 mm thick. A PDMS replica and a glass piece can each be oxidized for about 1 min in a plasma cleaner (for example, Harrick, PDC-001) prior to being immediately brought into contact with one another to achieve sealing of the channels in the PDMS replica to the glass piece. In this exemplary embodiment or in any other aspect of the invention, a device, e.g., a microfluidic channel, can be fabricated with glass, silicon, or polymeric materials using methods like dry etching, wet etching, laser processes, rapid prototyping, and traditional machining, using methods that are well known to one of ordinary skill in the art. In one aspect of a system of the invention comprising a microfluidic device, least one fluidic chamber or channel is required. Multiple chamber or channel arrays can also be provided for multiple simultaneous experiments.

Figure 2:
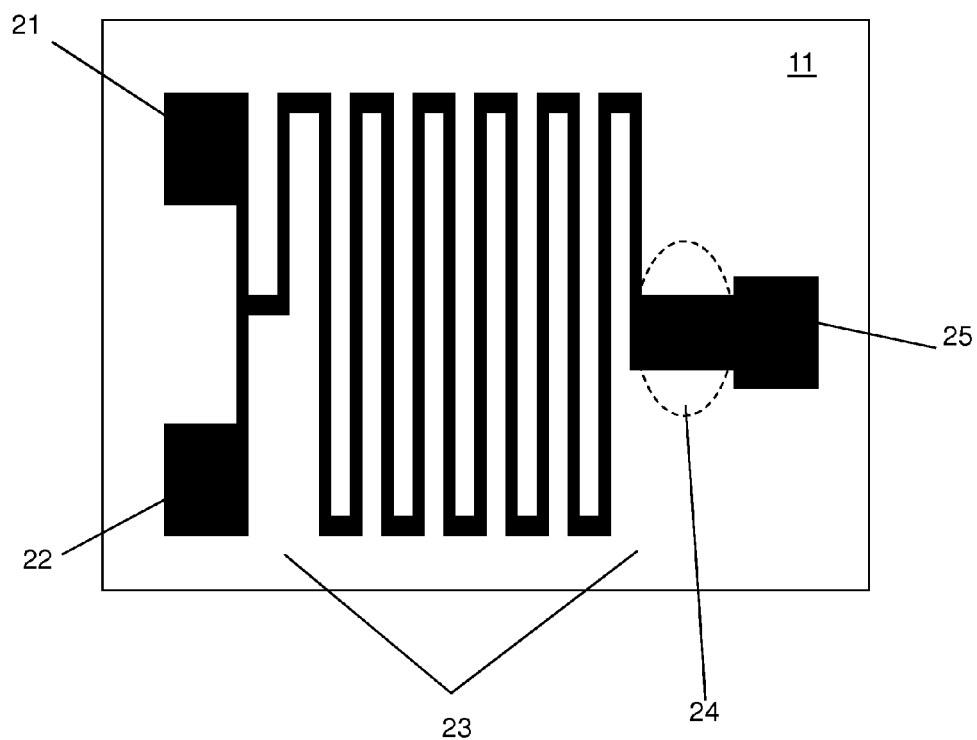
FIG. 2 illustrates an exemplary microfluidic bioreactor according to an embodiment of the invention.

FIG. 2 illustrates a top view of a microfluidic cell culture device 11 according to one embodiment of the invention. The cell culture is maintained in channel portion 24 for purposes of some examinations and sensings. Meandering channel section 23 is provided to mix inputs 21 and 22. Input 22, for example, can be used to introduce growth medium, without any experimental factors, and input 21, for example, can be used to introduce growth medium with a known concentration of an experimental factor. The flow rates of media into inputs 21 and 22, as well as the design of meandering channel section 23 can be set to provide desired temporal or spatial gradients to channel portion 24.

To sustain the cells and tissue samples for periods of ti me, a bioreactor, e.g., the exemplary microfluidic cell culture (bio reactor) device, can be loaded inside a closed chamber (e.g., Instec Inc, HCS60-STC20A) with temperature control, and adjusted to about 37° C. or some other selected temperature for the duration of the experiment (unless, of course temperature is an experimental variable, in which case the temperature could be varied in a controlled fashion over the course of the experiment). In one embodiment, the chamber can be filled with 5% of $CO_2$ mixed with air for maintaining the pH value of the medium. The diffusivities for O2 and CO2 in PDMS are about $4.1\times10^{-5}$ and $2.6\times10^{-5}$ cm$^2$/sec respectively, so the ambient atmosphere can affect the solution within the microfluidic bioreactor.

Figure 3:
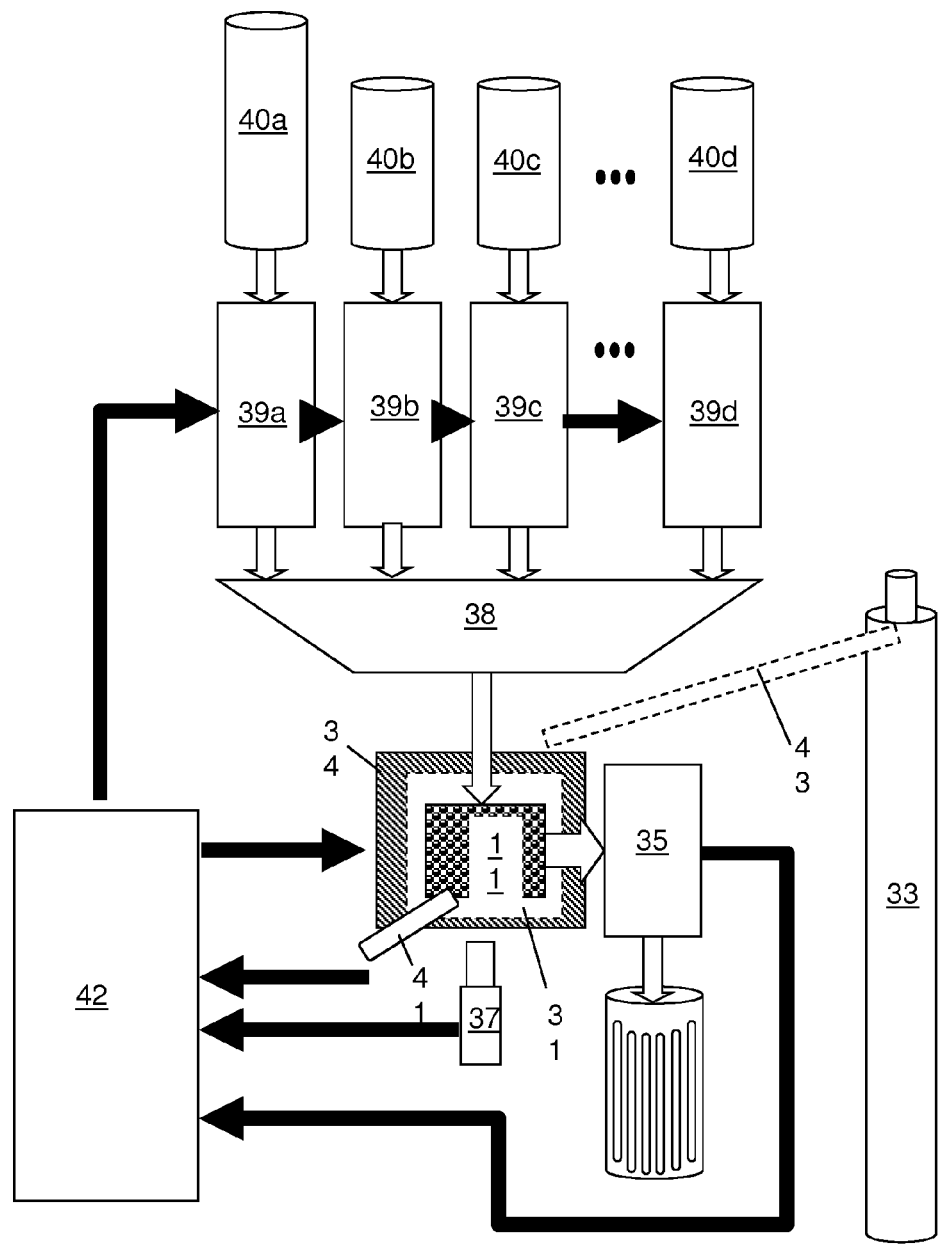
FIG. 3 illustrates an exemplary embodiment of the invention at an intermediate level of detail.

The embodiment illustrated in FIG. 3 shows microfluidic bioreactor 11 mounted within cavity 31 of closed chamber with temperature control 34. The temperature can be controlled by controller 42 responsive to temperature sensor 41 that is operable to measure a temperature of microfluidic bioreactor 11. A pressure sensor (not shown) can also be positioned to monitor pressure within the microfluidic bioreactor. Gas supply 33 supplies gas to cavity 31 of closed chamber with temperature control 34 via conduit 43. Mixing manifold 38 combines one or more incoming media solutions 40a-40d (for an example of four) via valves or metering pumps 39a-39d (again for an example of four) in a measured way.

In alternative aspects, the systems of the invention can comprise use of various media solutions and devices for controlling input and output of solutions; for example, different incoming media solutions can contain different chemicals and concentrations for either experimental or manufacturing purposes. The valves or metering pumps 39a-39b can be under the control of controller 42, which can thereby adjust the composition of the media being supplied to bioreactor 11. Although mixing manifold 38 has been pictured as separate from microfluidic bioreactor 11 in the embodiment as illustrated, mixing manifold 38 can be integrated with microfluidic bioreactor 11, for example as discussed above in relation to FIG. 2. Such embodiments can provide an advantage in that the mixed media can be substantially pre-equalized in temperature with the temperature of the bioreactor. In the embodiment of FIG. 3, the media effluent from bioreactor 11 can pass through sensor block 35, that can comprise sensors for metabolites, pH, or other chemical compounds for sensing purposes, that report back to controller 42. For the embodiment of FIG. 3, the media effluent is discarded after passing through sensor block 35. In other embodiments, the media effluent can be recirculated through the bioreactor. Although media effluent sensor block 35 has been illustrated as separate from microfluidic bioreactor 11, at least some of the functions of media effluent sensor block 35 can be implemented within microfluidic bioreactor 11, for example using electrochemical or spectrophotometric sensors. In the embodiment of FIG. 3, a camera 37 is optionally included and operably connected with controller 42. Camera 37 can be positioned to provide images of a biological sample within bioreactor 11 through a window in closed chamber with temperature control 34.

Figure 4:
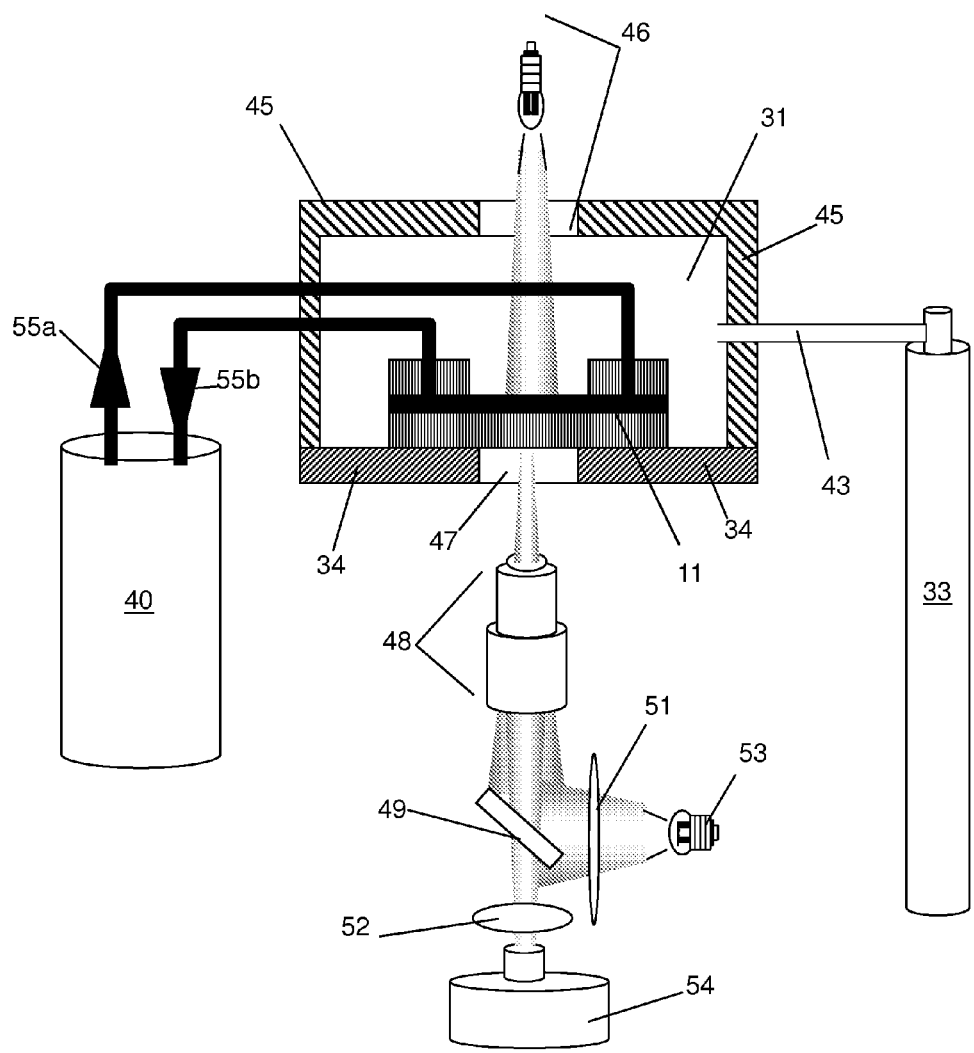
FIG. 4 illustrates another embodiment of the invention, showing fluorescent and phase contrast microscope sensors.

In some embodiments, a bioreactor (e.g., the exemplary microfluidic bioreactor) can be mounted on a fluorescence microscope, such as Nikon TE200 or TE2000, for real-time monitoring such as illustrated in FIG. 4. In this embodiment, bioreactor 11 is positioned above window 47 in temperature control stage 34 of sealed chamber 45. Atmosphere within sealed chamber 45 can be provided by gas source 33 via conduit 43. For simplicity of illustration, media inflow 55a and effluent 55b are shown as being recirculated through media reservoir 40. Drawing elements 48 through 53 illustrate a confocal fluorescent microscope of the type that is well known to one of ordinary skill in the art. Light source 53 shines through excitation filter 51 to dichoric beamsplitter 49, that directs a portion of the light through object lens assembly 48, that projects it on a biological sample in the bioreactor. Fluorescent emissions from the sample return through objective Jens assembly 48, through dichroic mirror 49, and through emission filter 52 to image capture device 54. Fluorescence images can be captured, for example, with a 1024× 1024 pixel, 16-bit cooled CCD camera (Photometric CH350L). Window and light source 46 schematically indicate a provision for including bright field and phase contrast microscope optics in additional embodiments of the invention.

Referring again to FIG. 3, in some embodiments, mini peristaltic pumps (Instech Inc, P625-1 0638) can be used for metering media inflows. A pressure transducer (Honeywell, ACSX05DN for example), and a temperature probe can be operatively coupled to the bioreactor and monitored by a controller (for example a personal computer with Labview software from National Instruments). Fluidic connection(s) of a bioreactor used to practice the systems or methods of the invention can comprise providing for fresh medium, recirculation of medium, removal—processing—and replacement of medium (e.g., to harvest a product, such as a recombinant protein, or a small molecule), removal of old medium or detoxifying medium, biochemical stimulation (e.g., with drugs, cytokines, hormones, etc), or mechanical (shear stress, pressure etc) control.

Figure 5:
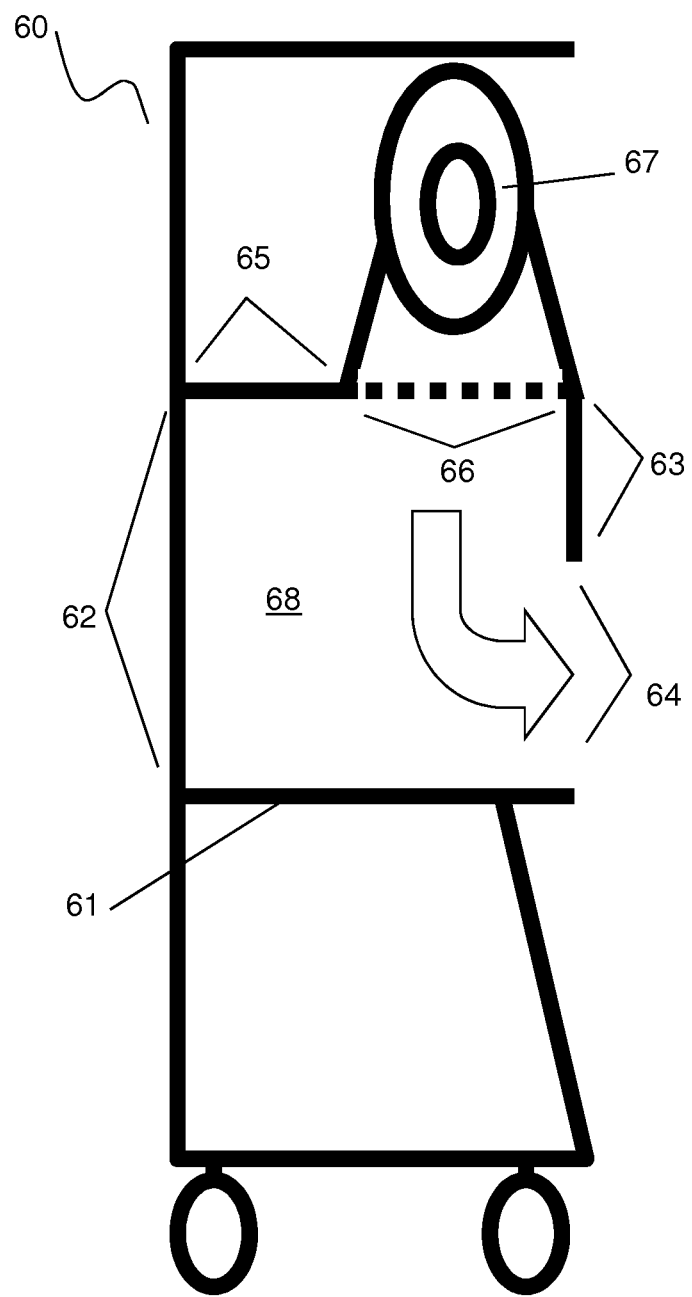
FIG. 5 illustrates an environmental enclosure for some embodiments of the invention.

Embodiments can be operated within a vertical clean bench such as shown in FIG. 5 to minimize contamination from the external environment. In the embodiment of FIG. 5 (shown in side cross-section), the requisite apparatus can sit on platform 61 within cavity 68 that is partially formed by platform 61, back wall 62, partial top wall 65, HEPA filter 66, partial front wall 63, and first and second side walls that are not shown. A blower 67 can be operably connected above HEPA filter 66 to direct a filtered flow of air downward toward platform 61 and outward through front aperture 64 in a substantially laminar flow. Because positive pressure is maintained within cavity 68, contamination by unfiltered outside air can be minimized even though front aperture 64 remains open for access. Such a system can allow long term cultivation of cells and tissue samples with low contamination by outside particulate matter and organisms.

Different embodiments can be used for sustaining and growing biological samples and providing stimuli. For example, in a perfusion or microfluidic cell culture embodiment, as described above, fluids can be continuously flowed through the bioreactor to recirculate medium, provide fresh medium, and/or dispense chemical reagents responsive to the controller. Alternatively, biological samples can be stimulated and monitored at discrete time points, responsive to the controller. In such embodiments, biological samples can be replaced in between iterations of the processes of the invention, and the medium can be maintained in a static condition in the between experiments. In such embodiments, other bioreactor devices, such as tissue culture dishes, Petri dishes, culture flasks, and multi well plates, can also be used with the invention; in one aspect, proper conditions, such as gas concentrations, pH values, and temperatures, are provided and/or maintained. The cell culture conditions can be provided and/or maintained by externally placed devices, such as with an incubator and/or other type of perfusion chamber. The conditions can also be generated and/or maintained internally with integrated devices within the bioreactor. Cells and tissue samples can be attached on a surface of the bioreactor. Alternatively, suspension cells can also be circulating in the bioreactor. A peristaltic pump, a syringe pump, or a pressure source can be used for driving the fluid motion, as are well known to one of ordinary skill in the art. Alternatively, integrated micro pumps such as chemical, mechanical, or electrokinetic pumps such as widely reported in the open literature covering nanotechnology developments can be used for generating fluid motion.

Perfusion manufacturing or experiment embodiments allow for the dynamic application of stimuli, such as drugs, inside a device, e.g., a bioreactor, such as a microfluidic bioreactor. However, such fluid flow can create shear stress on channel sidewalls of the device (e.g., a microfluidic bioreactor). Such shear stress can increase at the relatively small channel dimensions encountered in some microfluidic bioreactors. Cells in such microfluidic bioreactors can experience shear stress. This can be taken into consideration when designing manufacturing processes or experiments according to various embodiments of the invention. Various types of cells have been characterized for response to such shear stress. The cellular mechanisms for sensing the shear stress are generally unknown, but in designing systems of the invention it can be taken into consideration that most shear stresses that can induce biological response changes are of the same order of magnitude, about one to ten dynes/$cm^2$. The minimum shear stress for inducing a change in a cell can be cell-type specific. Shear stresses that are one to two orders of magnitude smaller than shear stresses known to elicit physiological response changes can be used as controls for different in vitro experiments or manufacturing processes or other experiments (e.g., cell-based, ex vivo) according to various embodiments of the invention.

Various embodiments of the invention provide different types of actuators to stimulate biological samples under test. Various embodiments of the invention provide stimulation in space and time. Various embodiments of the invention take into consideration fundamental cell processes such as cell motility, proliferation, and development, which are regulated by spatial and/or temporal stimulations, either biochemical or physical. For example, the upstroke rate of a pulsatile flow has been reported to affect the gene expression and remodeling of artery endothelial cells. In general, failure to regulate growth, to control differentiation, or to establish the proper morphological connections can cause many pathological conditions. However, traditional cell cultivation techniques have only limited capabilities to investigate such factors.

The ability to produce and apply these diverse stimulation landscapes with long-term monitoring using systems and methods of the invention is advantageous to cell study. Embodiments of the present invention can determine the proper control input parameters to induce desired biological responses, emulating natural signals, and/or therapeutic regimens that can regulate biological processes. Therefore embodiments of the invention provide actuators for generating such stimulations and/or environment signals. In some embodiments, actuators can generate stimulation with spatial and temporal resolution relevant to a biological process of interest, and can be automatically modified by the controller executing an optimization or search algorithm. For example, using microfluidic techniques as discussed above, transient stimulation can be generated with different cytokines. Concentration or duration of cytokine stimulation can be adjusted. Implementation of a microfluidic channel for cellular study can dynamically alter the cell culture medium, and temporal control of the chemical stimulants can be achieved.

In various aspects of the invention, bioreactors, e.g., microfluidic bioreactor embodiments of the invention, chemical/environmental stimuli that are measured, controlled—manipulated and/or induced include, without limitation, drugs, cytokines, soluble factors, dissolved gases, extra-cellular matrices, cell-cell interactions, neurotransmitters, and various ions—in steady state, or in temporal and/or spatial gradients. In some embodiments, a spatial chemical concentration gradient call be achieved by merging of two fluid streams, e.g., in a microchannel(s) of a device of the invention, so that molecular diffusion can occur between them. In some embodiments, a zigzag channel can extend the fluid path and hence the diffusion time for developing an approximately linear concentration gradient. A spatial chemical gradient of such embodiments can be characterized by merging streams of a dye, such as fluorescein, and another fluid, such as DI water. The concentration gradient of dye intensity can be experimentally determined by measuring the intensity profile downstream in the channel. A concentration gradient can also by estimated by finite element simulation considering the convective/diffusive transport of the molecules.

In addition to various chemical stimuli, some embodiments of the invention can provide physical stimuli such as mechanical forces, nano- or micro-structure environments, physical confinement, light intensities and wavelengths, temperatures, magnetic fields, and electric fields to study responses of a biological sample. For instance, a shear stress gradient can be generated at an interface of two microchannel cross-sectional areas and/or geometries. In a first embodiment, sudden enlargement of a straight channel produces a shear stress gradient around the corner of the junction, whereas distal regions of the enlarged section experience lower shear stresses which may be optimal for the culture of particular cells that can be immobilized in such a distal region. A different velocity landscape can be produced in a second embodiment having a converging channel. With a constant volumetric flow rate, the narrowing of the channel increases fluid velocity in the direction of flow which effectively decreases the shear stress field.

When the ranges of stimuli or environmental parameters that a biological sample can tolerate, such the concentration of a generated recombinant polypeptide, such as an antibody or a cytokine, or small molecule, or the magnitude of a mechanical force, or the concentration of cells in a culture system, are not known in advance, excessive stimulation or exposure, such as overdose or toxicity, may induce harmful effects to the samples. Moreover, the history of stimulation can also play important role in subsequent responses of biological samples. In such cases, various embodiments of the invention can use different biological samples of the same type, such as different batches of cells from a common culture, at different iterations of a study or a manufacturing process.

Some embodiments incorporate perfusion systems (e.g., microfluidic perfusion systems) in a bioreactor to practice the invention, e.g., for performing dynamic stimulation and real-time monitoring of biological samples to optimize or manipulate a biological sample, e.g., production of a biological product. Sensors can measure not only the magnitude of responses but also the dynamic nature of the responses. In some embodiments, such sensors can have high resolutions; for example, down to the single cell or sub-cellular level. Such capability provides information in sub-cellular processes, intercellular variations, population distributions, and ensemble averages. In some embodiments, the bioreactor for sustaining and stimulating the biological samples is integrated with sensors to allow the measurement cellular behaviors such as cell cycle, morphology, size change, proliferation rate, apoptosis rate, fusion rate, intracellular process. Such embodiments can be very useful for the study of cell dynamics, or manufacturing processes where cell dynamics is important for productivity, particularly where real-time monitoring is required. The dynamics of transcription factor activity, gene expression, cell proliferation rate, and apoptosis rate in biological samples also can be measured and/or manipulated when practicing the systems and methods of the invention. For example, in microfluidic bioreactors of the invention, manufacturing processes or experiments can be performed to investigate or manipulate the dynamics of transcription factor activity, gene expression, cell proliferation rate, and/or apoptosis rate in biological samples.

In alternative aspects of the invention, cell induction procedures are performed through non-invasive monitoring techniques, such as the use of reporter genes. For instance, the transcription activity of a cell can be monitored using green fluorescence protein (GPF) reporter. In various embodiments, sensors can measure the biological responses and the states of the system continuously, or at discrete time points.

In various embodiments, sensors used to practice the invention can include the following types, without limitation; fluorescent (e.g. ratiometric, intensity, fluorescent decay rate, photobleaching rate, photobleaching after fluorescence recovery); optical (e.g. optical density, colorimetric), electrical (e.g. impedance, current etc.); pressure; temperature, and chemical or biochemical. In various embodiments, sensors used to practice the invention can measure cell response to any internal or external stimuli by, e.g., regulating gene expression associated with various cellular processes such as proliferation, differentiation and signaling. The systems and methods of the invention can incorporate biotechnologies for real-time screening of gene expression in living cells with any tools, such as a reporter gene (GFP). The systems and methods of the invention can incorporate micro/nano fabrication technology to optimize microenvironments for manufacturing processes, or for experiments, e.g., for single cell studies.

For example, in one aspect, the gene expression dynamics of transcription factor NF-κB and the house keeping gene beta-actin in HEK 293T cells can be screened at the translational and transcriptional level, respectively. To monitor NF-κB dynamics, the destabilized green fluorescence protein (d2EGFP, BD Biosciences, Rockville, Md.) can be utilized as a reporter gene.

The systems and methods of the invention can also incorporate use of oligonucleotide probes, e.g., molecular beacons, which are oligonucleotide probes that have stem-and-loop structures and will undergo a spontaneous fluorogenic conformational change upon hybridization to a complementary nucleic acid target. For example, an oligonucleotide probes, e.g., a molecular beacon, can be used to monitor message RNA dynamics, e.g., the beta-actin mRNA dynamics measured in this example. Such a molecular beacon can be extremely specific and sensitive. A molecular beacon specific to any mRNA, e.g., the beta-actin mRNA, can be designed with the help of tools available in the public domain such as Basic Local Alignment Search Tool (BLAST) by National Center for Biotechnology Information (NCBI), mfold and RNAstructure programs. The characterization of the designed molecular beacon can be conducted with the ICY-CLER™ (iCycler iQ™) real-time PCR detection system.

In some embodiments, the sensor measurements are used that are non-invasive to the biological samples and the biological system represented by a biological sample returned to its original state after each stimulation iteration. In various embodiments, sensor measurements are used that are invasive procedures, such as, for example without exclusion: cell lysing; transfection; permeabilization of cell membranes; intracytoplasmic injections; illumination with electromagnetic waves; application of radioactive elements; application of fluorescent labeling; fixation; and flow cytometry. These invasive procedures can occur in between discrete measurements, or during continuous measurement and/or real time monitoring procedures. Such invasive procedures may induce unwanted effects on the system and should be eliminated or minimized. In some aspects, as appropriate, a sample subjected to such invasive procedures should not be reused during a subsequent test iteration. In some embodiments multiple samples of the same type can be started in parallel testing. At each test iteration, one of the samples is invasively measured and then discarded, with the iterative testing being continued with the other samples. In this way, measurements can then be done on samples that have not been invasively treated at each iteration, but otherwise share a common history.

Because the responses of a biological sample under stimulation can occur after a time delay, the measurements in the systems and methods of the invention can incorporate time delay(s). The systems and methods of the invention can take into consideration the fact that time delay(s) from stimulation to response for any particular biological sample can be an intrinsic property of that sample, result from the type or magnitude of stimulus, and/or depend on the history of the biological sample. In the control and optimization systems of the invention, the delay in time response can be considered as latency of a control problem. While characterization of a biological system's response time itself can be useful information for inducing a desired response, such information can be difficult to determine. In such a scenario, the response time itself can be considered as system parameter in the optimization processes and systems of the invention.

Systems and methods of the invention can use optimization or a smart search algorithm. These algorithms can be used to process information from biological sample sensor(s) to adjust stimulators. The algorithms can adjust information for combinations of stimuli to manipulate a response from a biological sample, or, to determine, measure or produce a more optimal response from a biological sample; this processing can be in a closed-loop fashion. Systems and methods of the invention can use information technologies, such as smart search algorithms, to organize and manipulate data resulting from measurements of responses in complex biological networks, or generating stimuli to complex biological networks (which include most bioreactor systems). Systems and methods of the invention can use focus on identifying individual components in biochemical and molecular biological systems and their interactions through signal transduction pathways. Systems and methods of the invention can use knowledge about complex biological systems to design and apply optimization strategies, e.g., from the field of engineering. Systems and methods of the invention can consider combinations of stimuli and their interactions in a desired biological system response. In this aspect, the technology is fundamentally different from the traditional approaches of conducting biological research in which each the effect of stimulus tends to be studied independently.

Embodiments of the present invention take a systematic approach to the regulation of complex biological systems, based on responses of a biological sample to different combinations of stimuli. In some aspect, rather than conducting numerous experiments to sample a multidimensional, multivariable stimulus space, and then processing response data to seek combinations of stimuli resulting in more desired responses, the systems and methods of the invention process response data to direct the combinations of stimuli used for subsequent manufacturing processing steps (e.g., iterative steps), or experiments, to generate subsequent data or manufacturing protocols. This can reduce the number of developmental manufacturing processing steps, or experiments, required for optimization by avoiding conducting experiments in unpromising directions. In some embodiments, a stochastic search algorithm, iteratively determines the inputs (stimuli) for achieving a desired response of the system (biological sample). Such embodiments go beyond using feedback and control for maintaining sustaining conditions for a biological sample, as is known in the art, by using feedback and control to control the selection of stimuli for experiments.

Any known stochastic search algorithm can be used in practicing the systems or methods of the invention; and examples of well known stochastic search algorithms include, without exclusion: simulated annealing; stochastic local search; stochastic hill-climbing; Metropolis-Hastings sampler; greedy randomized adaptive search; evolutionary algorithm; genetic algorithm; taboo search; and/or Gur Game, or variations or combinations thereof.

As discussed below, we have demonstrated Gur Game as an effective stochastic search algorithm in practicing the methods of the invention; see Examples below, for a study of cytokine combination optimization. Much like a genetic algorithm, the Gur Game aims for self-organization and self-optimization of the system. The essence of the Gur Game, including the forms used in practicing the invention, is a biased random walk toward the global optimum.

The essential concept in the Gur Game, including the forms used in practicing the invention, is the global figure of merit, called the reward function, which measures the performance of the system as a whole. To implement the algorithm, each input (e.g. a cytokine) is represented by an automaton with a pre-defined set of discrete states. In general, there is no specific limitation on the choice of the states in the automaton and different in puts can have different number of states and state values. During the study, each automaton move from one state to another based on being rewarded for their behavior. This "reward" probabilistically drives the system to the desired output states. More specifically, the output value (reward value) is compared to a random number. If the reward value is larger than the random number, the automaton is rewarded. Otherwise, the automaton is penalized. In other word, the reward values determine the chances that an automaton is "rewarded" at different iterations. This process is repeated for each actuator during each iteration. Eventually a global optimal state is achieved.

Modifications or variations of a Gur Game, multiple output, multiple reward values, and multiple set of measurements can be used to practice the invention. In one aspect, the predefined set of discrete state values can be changed dynamically according to the current or recent inputs and outputs relationship. In one aspect, the time period of each iteration can be changed dynamically. As noted above, other algorithms used to practice the invention include smart non-linear optimization search algorithms such as simulated annealing, stochastic local search, stochastic hill-climbing, metropolis-Hastings sampler, and variations thereof.

An advantage of stochastic search algorithms are that only minimal prior knowledge of the system to be optimized is required and the controller can calculate subsequent iteration in puts rapidly. The exemplary simulated annealing, stochastic local search, stochastic hill-climbing, Metropolis-Hastings sampler, greedy randomized adaptive search, evolutionary algorithm, genetic algorithm, taboo search, Gur Game algorithms are all exemplary sampling stochastic search algorithms that can be used to practice this invention, and all are well known in the art. Stochastic search algorithms have been shown to be effective in a variety of applications in science and engineering as reported in the open literature. In one aspect, a stochastic search algorithm can include at least one system performance goal, such as a reward function, which an algorithm attempts to optimize (e.g. minimize, maximize or to reach a constant value). This defines a goal for overall system performance. Other aspects use algorithms for driving a system towards better output, such as, for example, local gradient, probability of an event, or "evaporation" of certain parameters. A stochastic search algorithm used to practice this invention can also include randomness in directing search. Such randomness, can enable the algorithm escape from a local optimum when there could be a better local or global optimum. Avoiding entrapment in local optima can be especially important in searching complex biological systems that tend to be noisy, stochastic, active, and/or dynamical. Such randomness in a search algorithm can provide a generalized way to handle such unknown and unpredictable issues. Embodiments of the invention comprising stochastic search algorithms can be especially useful for studying living biological systems, unlike other biochemical systems where randomness is not as important.

Various embodiments can employ various methods to implement this random decision making. The randomness itself can be within a certain range, adjusting according to a pre-defined way, or adjusting according the dynamic response of the system's parameters.

Other control schemes can be incorporated into other embodiments for studying biological samples. Such control schemes can be classified by the level of prior knowledge required in order to implement the algorithm.

In one model-based control used to practice this invention, a physical system (a plant, in control terminology) is used, as described by a mathematical model. Then a controller, e.g. LQR (linear quadratic regulator) or PID (proportional-integral-derivate), can be designed according to the output requirements. In one aspect, among all the available control schemes, a model based controller can provide the best performance assuming the system is described reasonably accurate by the model and all essential components are considered. However, it can be difficult to regulate unknown signal transduction networks by using model-based controller without an adequate model.

Another type of controller used to practice this invention involves identification of the model and the model parameters. For example, neural network (NN) and design of experiment (DOE) type controllers belong to this category. In general, the more unknown parameters, the more data is required by the controller. In one aspect, as in a typical biological network, the system of the invention uses a large number of dynamic parameters. The fitting parameters are mainly determined by minimizing the deviations between measurements and model predictions. If the basic structure of network is known or large amount of data is available, the identification approach can be extremely useful. For example, in one aspect, techniques such as neural network are used to predict and control highly nonlinear systems. However, the identification methods could be misleading for certain networks and over-fitting can occur when high quality experimental data is not available.

Another category of controller used to practice this invention is rule based techniques, such as local search and stochastic search algorithms, such as described in more detail, below.

In practicing the invention, when using stochastic search algorithms, the system for optimization or manipulation can be a response (or set of responses) corresponding to a respective set of stimuli for discrete iterations. In one aspect, the stimulation to response time interval for a system for optimization or manipulation can be small compared to the interval between iterations, this pairing of data can uniquely characterize a system at each iteration. On the other hand, if the time interval is Jong compared to an iteration, the system's memory of prior stimuli can affect its response to present stimuli. In such cases dynamical or "analog" implementations can be used; i.e. the system itself determines the proper input waveform/duration and output measurement time. The resulting dimensionality of search space can, however, significantly increase in such cases.

The terms optimum, optimized, and optimization as used herein can refer to an improved, or more desirable biosystem response, even though the response may actually not be at an absolute optimum.

Computer Systems and Computer Program Products

The invention provides articles (e.g., computer program products) comprising a machine-readable medium including machine-executable instructions, computer systems and computer implemented methods to practice the methods of the invention. Accordingly, the invention provides computers, computer systems, computer readable mediums, computer programs products and the like having recorded or stored thereon machine-executable instructions to practice the methods of the invention. As used herein, the words "recorded" and "stored" refer to a process for storing information on a computer medium. A skilled artisan can readily adopt any known methods for recording information on a computer to practice the methods of the invention. The methods of the invention can be practiced using any program language or computer/processor and in conjunction with any known software or methodology. Some embodiments can use analog, or hybrid analog/digital circuitry for feedback and control, such as for example, neural networks, in which the control algorithm could be "hard wired." The term computer product as used herein can refer to any of such above embodiments.

Another aspect of the invention is a computer readable medium having recorded thereon machine-executable instructions to practice the methods of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

The computer/processor used to practice the methods of the invention can be a conventional general-purpose digital computer, e.g., a personal "workstation" computer, including conventional elements such as microprocessor and data transfer bus. The computer/processor can further include any form of memory elements, such as dynamic random access memory, flash memory or the like, or mass storage such as magnetic disc optional storage. For example, a conventional personal computer such as those based on an Intel microprocessor and running a Windows operating system can be used. Any hardware or software configuration can be used to practice the methods of the invention. For example, computers based on other well-known microprocessors and running operating system software such as UNIX, Linux, MacOS and others are contemplated. As used herein, the terms "computer," "computer program" and "processor" are used in their broadest general contexts and incorporate all such devices.

The invention will be further described with reference to the following examples; however, it is to be understood that the invention is not limited to such examples.

EXAMPLES

The following examples are provided to illustrate, but not limit, embodiments of the invention. In the first example, nearly optimal combinations of cytokines are determined for regulating transcription activity. This example represents a use of an embodiment of the present invention for additional applications of the invention, e.g., vaccine production optimization, drug screening, determining therapeutic regimens for the treatment of diseases, toxicity studies, and the like. In the second example, another embodiment of the invention is used to direct activation and differentiation of neural stem cells for tissue engineering applications. In the third example, a method for manipulating and discovering artificial gene and metabolic networks is described. The third example illustrates the use of an embodiment the present invention to mimic and study biological processes.

Example 1

Optimizing a Combination of Cytokines to Regulate Transcription Factor NF-κB

As a first example, we applied the Gur Game algorithm (one of the exemplary optimization algorithms used to practice the invention) for regulating the activity of a polypeptide, a transcription factor called nuclear factor kappa B (NF-κB). This example demonstrates that the systems and methods of the invention can effectively measure and manipulate environmental parameters in a bioreactor, and manipulate and optimize a biological system (in this example, regulating the expression and/or activity of a polypeptide).

NF-κB regulates expression of numerous genes that mediate survival, apoptosis, proliferation, inflammatory response, and oncogenesis, and is reported to be one of the major drug targets for cancer and chronic inflammatory diseases. The NF-κB activity can be controlled by several signal transduction pathways and numerous stimuli can trigger the activities of one or more kinases that activate NF-κB. Determining a set of cytokines and growth factors that exerts desired effects on NF-κB can be a crucial step for realizing the therapeutic potential of targeting NF-κB. At the same time, the nonlinear interactions among the pathways and the large parametric space constituted by the combinatory cytokines impose a major challenge.

An advantage of an embodiment using the Gur Game as a search algorithm for implementation on the controller is that the Gur Game does not require an a priori model of the system. Gur Game can be robust and used to make random changes in the system and the environment. Therefore, exemplary systems and methods of the invention comprising use of Gur Game as an optimization algorithm is good choice for controlling complex biological systems for which adequate modeling of the governing networks is lacking. The Gur Game can be viewed as being based on biased random walks of multiple finite state automata toward higher system performance, as defined by a reward function. The asymptotic behavior of the automata has been modeled using the Markov chain analysis. The reward function of the system can be multi-modal, nonlinear, and even discontinuous.

Figure 6:
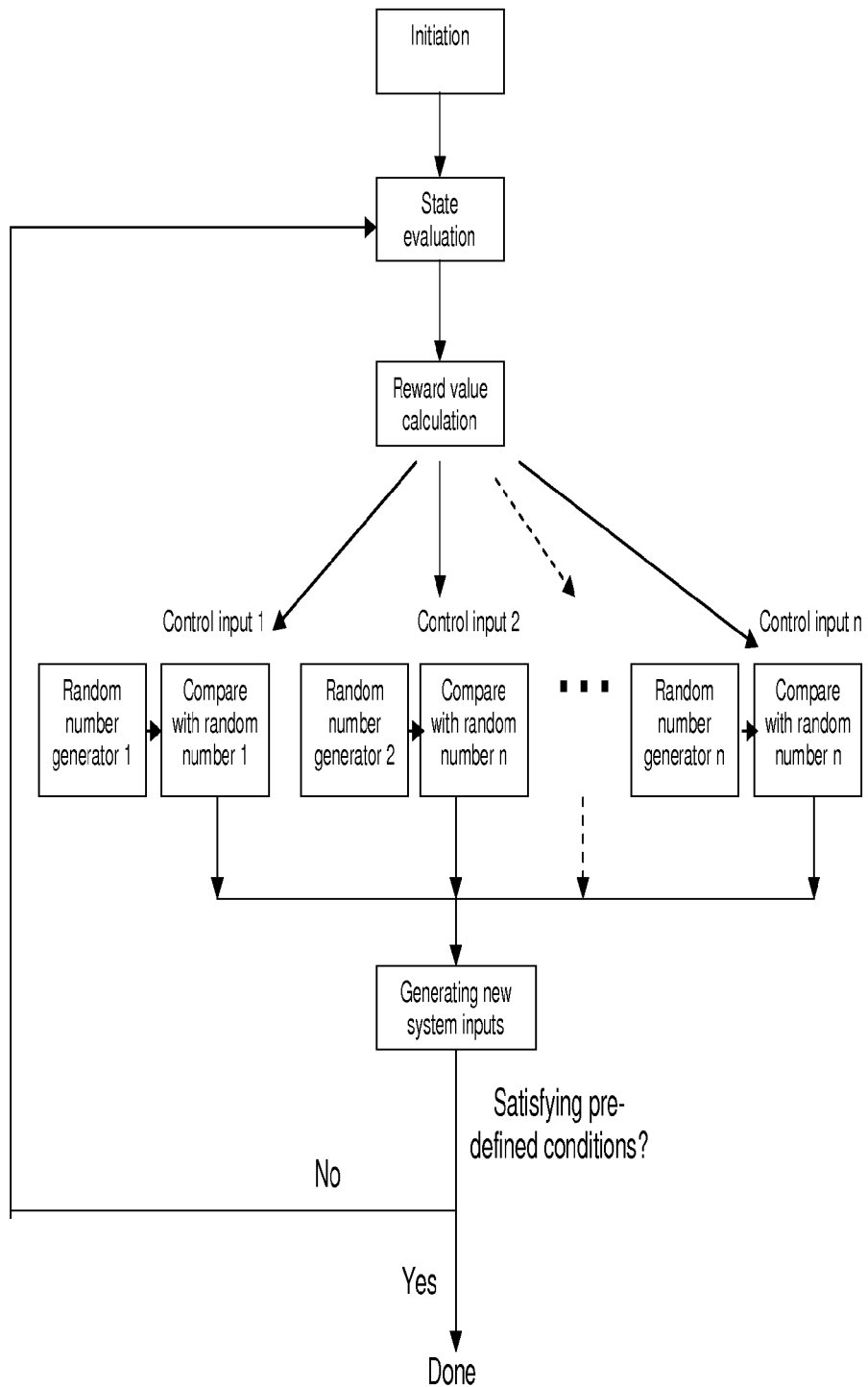
FIG. 6 is a flow chart illustrating an exemplary Gur Game search algorithm, according to an embodiment of the invention.

To implement the Gur Game algorithm, each cytokine was represented by an automaton with 10 discrete states (0, 0.25, 0.5, 1, 2.5, 5, 10, 25, 50, and 100 ng/ml) as shown in FIG. 6. At each iteration, a combination of cytokines at their respective states was applied to stimulate the cells for one hour. The transient response of GFP intensity was observed to approach a maximum at about seven hours after stimulation, coinciding with reports in the open literature. The choice of cytokines or combination of cytokines did not show an observable effect on the transient response of the fluorescence intensity. The GFP expression kinetics is thought to be controlled by protein folding and degradation rates, while the amount of transcription (GFP intensity) is thought to provide an indication of the NF-κB activity. The peak intensities were normalized as the reward function for Gur Game. The reward function maps the system state from 0 to 1, with high GFP intensity corresponds to values nearer 1. For each automaton, a random number from 0 to 1 is chosen and compared with the reward value. The next states of the automata were determined according to a prescribed manner (see FIG. 1). The process was repeated for each cytokine during each iteration.

Referring again to FIG. 6, each cytokine as represented by an automaton. The numbers represent the concentration of the cytokines, in ng/ml. During each iteration, a random number was generated for each automaton. The numbers were compared to the reward value. If the reward value was larger than the random number, the automaton was rewarded (win). Otherwise, the automaton was penalized (lose). The automaton then decided the state in the next iteration according to the automaton design. Generally, the state moves toward center if penalized, and away the center if rewarded.

Microfluidic systems have been proven to be effective for manipulating different biological objects, such as cells and molecules. In this example, the optimization experiments were conducted inside microfluidic channels to facilitate real-time monitoring and dynamic stimulation of the cells. At each iteration, the cells were transiently stimulated with a combination of agonists for one hour as shown in FIG. 7A. (In FIG. 7a, the concentrations of individual cytokines are indicated as follows: TNFα concentrations are plotted as solid squares; TNF concentrations are plotted as solid circles; IL-1α concentrations are plotted as solid triangles; IL-1β concentrations are plotted as inverted triangles; EFG concentrations are plotted as open squares; and BAFF concentrations are plotted as open circles.) The initial concentrations of the cytokines were 2.5 ng/ml. In order to monitor the activity of the NF-κB, a plasmid with a green fluorescent protein (GFP) reporter gene was placed in the 293T cell. The GFP expression is controlled by a promoter which consisted of a kappa enhancer element (KB4). Similar configurations have been applied in other studies where the GFP fluorescence intensity was able to reflect the cellular NF-κB activity. In addition, computational analysis was performed to correlate the relationship between the expression level of GPF and the activity of NF-κB. Numerical simulation indicated the best duration and time for cytokine stimulation and GFP intensity measurement. The GFP fluorescence intensity of each cell was recorded 7 hours after the stimulation as shown in FIG. 7B (data represent the average intensity of 40-128 cells).

The Gur Game was used to determine the cytokine concentrations in subsequent iterations to probabilistically drive the system toward a high GFP output, i.e. high NF-κB activity. FIG. 6 is a flow chart illustrating an exemplary Gur Game Algorithm, the algorithm used in this example. A detailed description of this exemplary algorithm is set forth above. The peak intensities were normalized as the reward function for this exemplary Gur Game algorithm. The reward function maps the system state from 0 to I, with high GFP intensity corresponds to values nearer 1. For each automaton, a random number from 0 to I is chosen and compared with the reward value.

Figure 7:
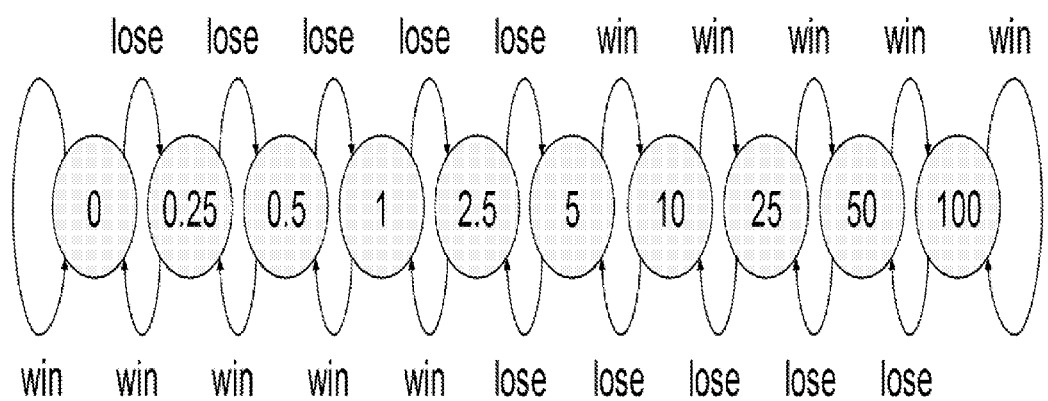
FIG. 7 shows a state diagram illustrating an exemplary Gur Game search algorithm that is used in an embodiment of the invention.

The next states of the automata were determined according to a prescribed manner, as illustrated in FIG. 7. The process was repeated for each cytokine du ring each iteration. Each cytokine as represented by an automaton. The numbers represent the concentration of the cytokines, in ng/ml. During each iteration, a random number was generated for each automaton. The numbers were compared to the reward value. If the reward value was larger than the random number, the automaton was rewarded (win). Otherwise, the automaton was penalized (lose). The automaton then decided the state in the next iteration according to the automaton design. Generally, the state moves toward center if penalized, and away the center if rewarded.

Figure 8A:
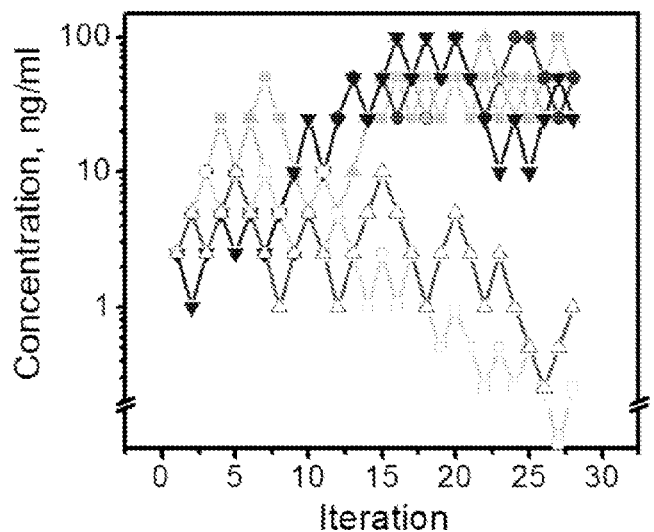
FIGS. 8A, 8B, and 8C illustrate a substantially optimal biological system response as generated by an exemplary system of the invention.
Figure 8B:
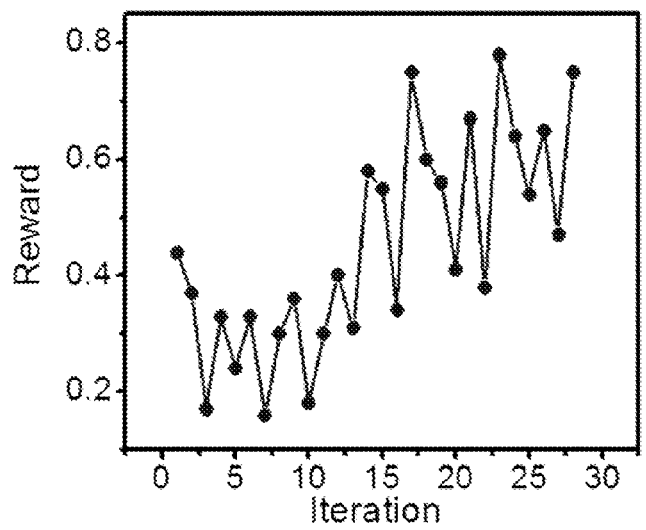
Figure 8C:
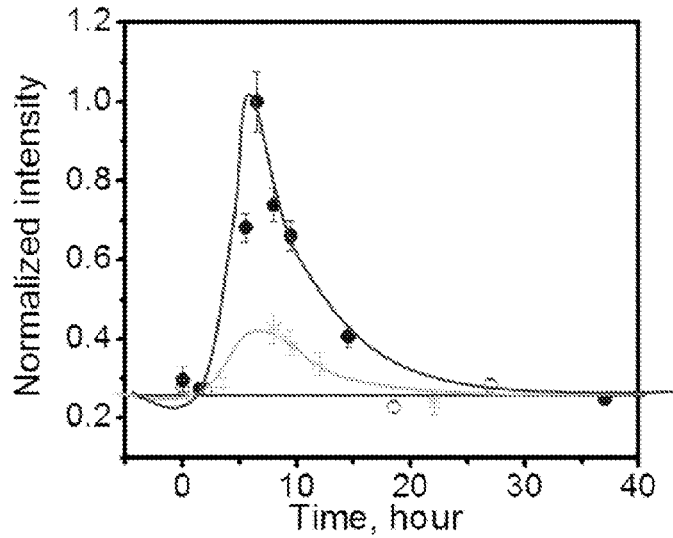

Referring to FIGS. 8a and 8b, initially, the system rejected several cytokine combinations with seemingly high outputs. At iteration 17, the system determined a potent combination of cytokines for activating the NF-κB signal transduction pathways. Due to the random walk nature of the Gur Game, the system did not settle even with the large performance gains at iteration 17. The algorithm continually searched for other states with better performance. It is seen that the reward function decreased significantly for several iterations during the search. However, the system robustly returned to the similar NF-κB activity at iterations 23 & 28. This most potent cytokine combination, which was determined by the final probability distributions of the cytokine concentration (see supplementary material), was TNFα.=25 ng/ml, TNFβ=50 ng/ml, IL-1α=50 ng/ml, IL-1β=25 ng/ml, EGF=2.5 ng/ml, BAFF=2.5 ng/ml. The robustness of the Gur Game algorithm is further illustrated by the observation that the paths by which the cytokine combinations moved toward the peak were different. In principle, an even larger parametric (input variable) space, e.g. 7, 8 or more cytokines with $10^7$, $10^8$ or more combinations, is expected to achieve a similar rapidly converging rate by using the stochastic searching in a feedback loop. FIG. 8C shows normalized GFP intensity at different iterations for the cytokine combination and individual cytokine (TNFα). In FIG. 8C, the dynamic responses of NF-κB activity for cells treated with the cytokine combination are plotted as solid circles, the dynamic responses of NF-κB activity for cells treated with TNFα 50 ng/ml are plotted as asterisks, and the control dynamic responses of NF-κB activities are plotted as open circles. Data represent the mean±SEM (standard error of the mean, numerically:

$$S_{\bar{x}} = \frac{S}{\sqrt{n}},$$

where S is the standard deviation and n is the number of measurements) from at least 100 cells inside the microfluidic channels.

Figure 9A:
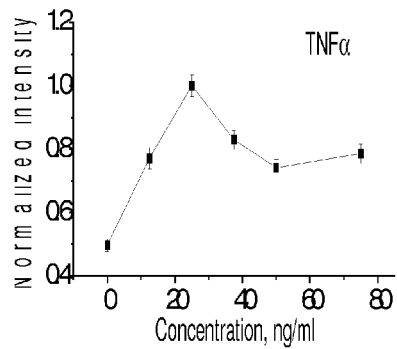
FIGS. 9A, 9B, 9C, 9D, 9E, and 9F illustrate a sensitivity analysis of individual cytokines in combination, as determined by an embodiment of the invention.
Figure 9D:
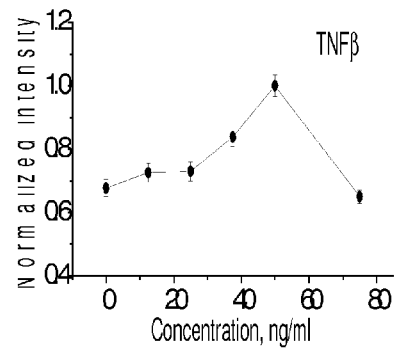
Figure 9B:
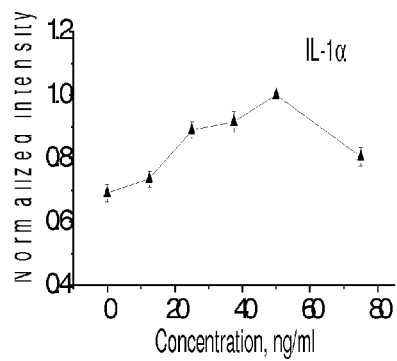
Figure 9E:
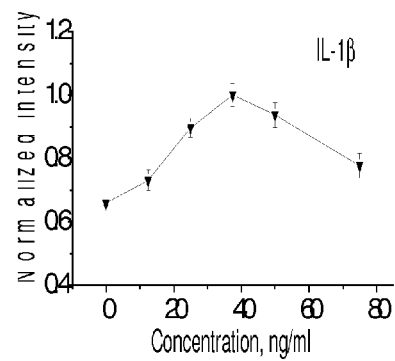
Figure 9C:
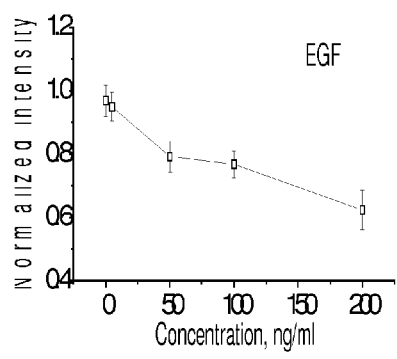
Figure 9F:
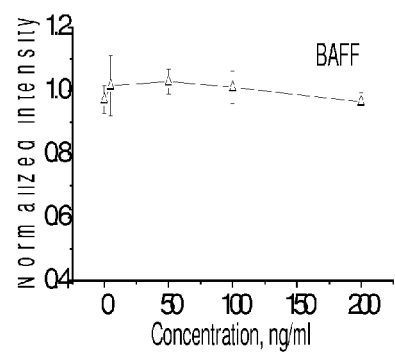

With the most potent combination of cytokines efficiently determined by the closed-loop feedback control scheme of the embodiment, the concentration of a specific cytokine was then varied, while the concentrations of the others were held constant to understand the sensitivity of the specific cytokine as shown in FIGS. 9A through 9F. For FIGS. 9A through 9F, the data show mean±SEM of at least 300 cells. Experiments were conducted in 96-well plates. The cells were stimulated with the appropriate concentration of cytokines for one hour and washed with fresh media. Fluorescence measurements were carried out 7 hours after stimulations.) TNFα was found to be the most sensitive in the combination in affecting the activity of NF-κB. Elimination of TNFα in the cytokine combination resulted in a ~50% decrease in fluorescence intensity. Total elimination of any one of TNFβ, IL-1α or IL-1β resulted in ~30% decrease in fluorescence intensity. The sensitivity curves of TNFα and β (FIGS. 9A and 9B) exhibited "peaky" patterns while the curve patterns for IL-1α and β (FIGS. 9C and 9D) were smoother. The effects of IL-1α and IL-1β were not sensitive to their concentrations in the range of 25-50 ng/ml. When combined with the potent cytokine combination, EGF decreased the NF-κB activity with increasing dose concentration (FIG. 9E). It should be noted that EGF alone did not show a strong effect on the NF-κB activity in 293T cells (data not shown). For the case of BAFF, it had a minimal effect on NF-κB activity with or without the potent cytokine combination (FIG. 9F). It is interesting to note that the Gur Game search algorithm suggested lower and lower concentrations of both EGF and BAFF as the iterations proceeded (FIG. 7A). These data clearly indicate that the effects of individual cytokines are not additive in the combinatory tests and the interactions among pathways are nonlinear.

Example 2

Directed Neural Stem Cell Differentiation with Biochemical and Physical Stimuli by an Intelligent Closed-Loop Control Algorithm As a second example of the use and effectiveness of an exemplary embodiment of the invention, the activities and differentiation of stem cells were investigated, specifically the activities and differentiation of neural progenitor cells (NPCs), which are promising areas for tissue engineering applications. This exemplary example demonstrates that the systems and methods of the invention can be used to determine parameters for the direction of cell behavior, e.g., stem cell behaviors. This example demonstrate that the compositions and methods of the invention can be used for systems manipulation and/or optimization of a biological manufacturing, cell engineering, or experimental systems related to cell behavior, including cell growth or differentiation, e.g., in bioengineering systems for reconstructing or regrowing tissue or organ systems, e.g., in nervous system, muscle or liver damage repair, or, in bioreactors for the production of proteins, polypeptides or peptides for vaccines; including manipulation and/or optimization of systems for differentiating cells to a desired state or having a specific property, e.g., ability to produce or modify a polypeptide, e.g., a therapeutic protein, polypeptides or peptides for vaccines, and the like.

A promising approach for treatments of nervous system damages is cell-replacement therapy. Several recent studies have been described in the open literature on transplantation of neural precursor/stem cells into the rodent model of spinal cord injury. While cell transplantation therapy has shown promises as a clinical treatment, the approach processes several concerns. For instance, transplantation of undifferentiated cells could result in low engraftment efficiency and therefore reduced clinical efficacy. Undifferentiated progenitor cells may cause spontaneous differentiation into undesired lineages. Most importantly, it processes the risk of teratoma formation, in the case of embryonic stem cells. Ex vivo differentiation of NPCs provides a promising alternative, which may minimize the previously mentioned concerns. For differentiation of neural cells prior to transplantation, the commitment could be overridden by environmental cues in the injured spinal cord. Large scale directed differentiation, separation, and purification of target cells still presents challenges. It is generally believed that more basic and preclinical research must be done before attempting human trials using stem cell therapies to repair the damaged nervous system. There are many fundamental questions still to be answered either for developing replacement cells or activating the body's own stem cells in vivo. An embodiment of the present invention provides a unique tool to determine parameters for the direction of stem cell behaviors.

One embodiment of the present invention can be used to systematically investigate the effects of cytokines, growth factors, extracellular matrix environment, and electrical activity on growth and differentiation. Similar to most biological systems, a stem cell's activity and differentiation can depend on a large number of exogenous parameters, in which stimuli, their respective magnitudes, their respective temporal and spatial gradients, and their interactions can be important to the determination of a differentiated phenotype and the fate of the differentiated phenotype. Embodiments of the present invention can mimic in vivo environments and search for optimum (or nearly optimum) stimulation to direct stem cells to desired expressions. With these apparatus and method embodiments, NPCs' physiology that is concerned with the cytokine stimulation, as well electrical activity associated with living cells and involved in their functional activity can be studied in a fast pace. Important mechanisms of NPCs response to cytokines and electrical activity, such as depolarization ion, electrodeformation, and associated signal transduction pathway can be studied in detail. Migration, proliferation, neurogenesis, and remyelization of NPCs under external electric fields, cytokine exposures, and ECM can be characterized. The information obtained can enable the selection of operating parameters of electrical and other biomedical stimulation in clinical therapeutic approaches, such as neural prosthesis, stem cell implantation, and stimulation of endogenous progenitor cells for the replacement of lost neural functions. ECM is extracellular matrix. ECM is a complex network of polysaccharides and proteins secreted by cells and a structural component of tissues that also influences their development and physiology.

In one aspect, cells can be obtained from human fetal tissue between 14 and 21 weeks post conception, and then cultured. NPCs can also be isolated and cultured from human brain tissue for the first several years of life. The NPCs can be cultured in (DMEM):HAMS F12 at about (50:50), gentamicin at about 30 mg/ml, amphotericin B at about 15 μg/ml, human recombinant basic fibroblast growth factor (FGF-B) and epidermal growth factor (EGF) both at about 20 ng/ml, and N2 at about 1:100.

Before each experiment, the cells are incubated in a approximately 5% $CO_2$ atmosphere incubator at approximately 37° C. for about 24 hours, allowing them to recover from cryopreservation prior to use in the adhesion and proliferation assays. The cells can then be cultured on a microfluidic bioreactor device, according to an embodiment of the invention. Actuators, such as micro- and nano-electrodes, extracellular matrices, growth factors, and differentiation factors, can be integrated into microfluidic bioreactor. These stimuli can be directly control with a computer serving as a controller. The cell's behavior, including migration, proliferation, and lineage specific markers (Tuj 1 for neuron, RIP for oligodendrocyte and GFAP for astrocytes) can be monitored in real time and continuously and served as biological responses from which reward functions (in Gur Game and other stochastic search/nonlinear optimization terminology). The information obtained in the measurement can then be fed into the Gur Game algorithm or other stochastic search algorithms to determine next iteration stimuli in the search for better combinations of stimuli for more nearly optimal responses. Synergistic and antagonistic effects of stimuli can also be studied in this way.

As described above, this embodiment of the invention can determine optimal (or nearly optimal) operating parameters of electrical and other biochemical stimulation to direct the neural progenitor cells to differentiate into cells with desired phenotypes. This can pave the way for novel treatments of degenerative diseases of the nervous system. One set of goals is to determine the proper conditions for the differentiation of NPCs to specific neural cells, such as oligodendrocytes and motor neurons, for SCI and ALS treatments. While direct differentiation of NPCs is clearly useful, other aspects of the neural activity can also be considered. In many spinal injuries, the spinal cord is not fully damaged and some of the signal-carrying neuronal axons are intact. However, the surviving axons no longer carry messages because oligodendrocytes are lost. One possibility is to direct the migration or directly implant neural progenitor cell to the injury site and stimulate their differentiation in situ into appropriate supporting cells, such as oligodendrocytes. Another possibility is to differentiate neural progenitor cells in vitro and direct the differentiated cells into the injury site. With various embodiments of the present invention, many important aspects of the neural processes can be investigated, including for example: (i) the migration of NPCs and glia cells; (ii) the survival and proliferation of NPCs; (iii) the differentiation of NPCs to specific cell types of the nervous system; and (iv) remylenation of differentiated oligodendrocytes.

Example 3

Iterative Methods for Discovering, Manipulating and Optimizing Natural and Artificial Gene Networks This example demonstrates that the systems and methods of the invention can be applied to design, manipulate, understand and/or optimize (or nearly optimize) natural and artificial gene and metabolic networks, including neural networks and similar biological systems, such as metabolic, growth, apoptotic or differentiation networked systems. This example also demonstrates that the systems and methods of the invention can be applied to mimic in vivo neural, gene and/or metabolic networks.

In nature, biological systems such as gene and metabolic networks have been observed to express themselves in various ways, such as circadian clocks and auto-regulated gene expressions, for example. It is of great interest to understand, control, and mimic such gene and metabolic networks both in living organisms (in vivo) and artificially (in vitro). However, such networks tend to be sensitive to a large number of intercellular factors (e.g. secreted factors, quorum, etc.), intracellular factors (e.g. genes, promoters, pathway components, etc.), and extra cellular parameters (e.g. carbon sources, pH, temperature, light intensity, and other biochemical reagents etc). Without a detailed understanding of such stimuli and their interactions, it is difficult to understand, control, and/or mimic the robustness, functionality, and properties of these metabolic networks. Embodiments of the present invention can obviate the need for a full understanding of metabolic networks, while indicating appropriate environment cues (stimuli)) for desired metabolic network responses.

Oscillatory networks in *E. coli* have been described in the open literature, however the role and influence of environmental cues (stimuli) remain unclear. An embodiment of the present invention can be used to determine external signals required to activate and/or modulate an oscillatory network (in this or any other system). *E. coli* can be cultured in microfluidic systems fabricated by micromolding of polydimethylsiloxane (PDMS) on photoresist master. In an embodiment of a microfluidic bioreactor, as described above. Poly-L-lysine (Sigma, P 8920) can be applied at desired locations in the microfluidic device using a pipette or a sharpened glass capillary to achieve selective cell depositions. Patterns on the order of 10 µm can be printed with this method. For instance, patterns of roughly 500 µm (field of view of the optical system) can be printed in order to trap multiple cells for statistical analysis. The channel can then sealed by a piece of cover slip. Before sealing, holes can be drilled on the glass for interconnections. The microfluidic channel can be washed by flowing phosphate buffered saline (PBS) for about 5 min. The solution can then be switched to about 10 mg/ml of bovine serum albumin in PBS for about 5 min. This process can reduce the non-specific binding of cells the in the channel. The channel can then be filled with a suspension of the *E. coli* cells and the cells are allowed to adhere to the channel surface for about 5 min. Cell adhesion occurs preferentially in regions with poly-L-lysine modification. The number of cells adhered on the channel surface can be adjusted by adjusting the cell concentration in the solution and residency time of the cells in the channel. Non adherent cells can then be removed by washing with culture medium.

The microfluidic chip (bioreactor, see FIG. 2) can be loaded onto an epi-fluorescence microscope (for example a Nikon TE 200™) equipped with an ultraviolet light source (e.g., a 100 W mercury lamp). A thermolectric hot and cold stage (e.g. Instec, HCS60 with a platinum RTD temperature control sensor) can be mounted on the microscope. This can be used to maintain the temperature of the microfluidic chip at about 37° C. with a PID feedback controller (for example, Instec, STC200™) for the gene expression experiments. The two inlets of the microfluidic chip (21 and 22 of FIG. 2) can be connected to reservoirs of desired fluids. A peristaltic pump (e.g., Instech, P625) can be connected at the outlet (25 of FIG. 2) for fluid aspiration. The configuration allows for substantially identical flow rates from the two inlets, thereby promoting the generation of a stable chemical gradient in zig-zag section 23 (FIG. 2) of the microfluidic chip 11. The flow rate can be adjusted from about 1-400 µl/min and can be calibrated with a pressure transducer (e.g., Honeywell, ACSX™ series).

Fluorescence and bright-field images can be imaged by, for example, a 16 bit, 1024 by 1024 pixel cooled CCD camera (such as a Photometric CH350UM) periodically at a predefined period of roughly 1-5 min intervals and recorded on an appropriate medium. Light sources can be shuttered between exposures. Approximately two to three hundreds cells can be captured in the field of view in one image. This embodiment can be combined with image analysis software for automated processing.

Spatial chemical gradients can be generated by merging streams of media and reagents of various concentrations. The concentration gradients of chemical can be experimentally determined by fluorescence intensity. Different concentrations of IPTG in M9 medium can be tested. The inducer concentration distribution in the gene expression experiment can be estimated by numerical simulation (CFDRC) with diffusivity $8.80 \times 10^{-6}$ cm$^2$/sec for IPTG at 37° C.

Stimuli, such as inducers, carbon sources, temperature, pH, cell densities; and internal gene circuit parameters, such as promoter activities, transcription rates, translation rates, maturation rates, and metabolic reaction rates, can be studied and tested with this embodiment. The biological sample outputs, such as GFP intensity, frequency, number of mitosis cycles, and cell-cell variations, can be monitored and recorded with a CCD camera in some embodiments. The Gur Game algorithm or other stochastic search algorithm can be applied to optimize (or nearly optimize) stimuli to elicit a desired response from the biological sample in various embodiments (for example, maximizing the frequency of GFP oscillation frequency) Since biochemical reactions can generally be speeded up by increasing temperature, it is likely that temperature is an important factor for the maximizing the frequency. Typically, bacteria are cultured at 30° C. to 37° C., which is a reasonable range for initial testing. However, increase in temperature may alter the dynamics of the reactions and overheat enzymes, thereby reducing their activities. The doubling rate, which affects the protein dynamics in a variety of ways, can also be changed. Other parameters, such as pH, can also affect a metabolite's transportation rates and other reaction kinetics and, therefore, the overall performance (frequency) of the gene network. In general, the critical parameters are unknown and the interactions of these parameters are unclear.

Embodiments of the present invention with a stochastic search algorithm can provide a systematic method for determining the optimal combination for maximizing the frequency and provide important insights for understanding the important parameters (stimuli) and their interactions.

It will be appreciated that the above description for clarity has described exemplary embodiments of the invention with reference to different functional units and processors. However, it will be apparent that any suitable distribution of functionality between different functional units or processors may be used without detracting from the invention. For example, functionality illustrated to be performed by separate processors or controllers may be performed by the same processor or controllers. Hence, references to specific functional units are only to be seen as references to suitable means for providing the described functionality rather than indicative of a strict logical or physical structure or organization.

The invention can be implemented in any suitable form including hardware, software, firmware or any combination of these. The invention may optionally be implemented at least partly as computer software running on one or more data processors and/or digital signal processors. The elements and components of an embodiment of the invention may be physically, functionally and logically implemented in any suitable way. Indeed the functionality may be implemented in a single unit, in a plurality of units or as part of other functional units. As such, the invention may be implemented in a single unit or may be physically and functionally distributed between different units and processors.

Although the present invention has been described in connection with some embodiments, it is not intended to be limited to the specific form set forth herein. Rather, the scope of the present invention is limited only by the accompanying claims. Additionally, although a feature may appear to be described in connection with particular embodiments, one skilled in the art would recognize that various features of the described embodiments may be combined in accordance with the invention. In the claims, the term comprising does not exclude the presence of other elements or steps.

Furthermore, although individually listed, a plurality of means, elements or method steps may be implemented by e.g. a single unit or processor. Additionally, although individual features may be included in different claims, these may possibly be advantageously combined, and the inclusion in different claims does not imply that a combination of features is not feasible and/or advantageous. Also the inclusion of a feature in one category of claims does not imply a limitation to this category but rather indicates that the feature is equally applicable to other claim categories as appropriate. Furthermore, the order of features in the claims does not imply any specific order in which the features must be worked and in particular the order of individual steps in a method claim does not imply that the steps must be performed in this order. Rather, the steps may be performed in any suitable order.

The figures provided are merely representational and may not be drawn to scale. Certain proportions thereof may be exaggerated, while others may be minimized. The figures are intended to illustrate various implementations of the invention that can be understood and appropriately carried out by those of ordinary skill in the art.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. A method for optimization of a response of a biological system, comprising:
    obtaining measurements of a biological system in response to varying concentrations of drugs in a drug combination;
    fitting the measurements into a model of the biological system; and
    predicting concentrations of the drugs in the drug combination to yield an optimized response of the biological system, based on a predicted response of the biological system according to the model.

2. The method of claim 1, wherein fitting the measurements includes determining multiple fitting parameters of the model.

3. The method of claim 2, further comprising:
    determining predicted responses of the biological system to varying concentrations of the drugs;
    obtaining measured responses of the biological system to the varying concentrations of the drugs; and
    determining one or more of the fitting parameters by reducing deviations between the predicted responses and the measured responses.

4. The method of claim 1, further comprising:
    determining optimized concentrations of the drugs based on the model; and
    directing the optimized concentrations of the drugs to be applied to the biological system.

5. The method of claim 1, further comprising:
    selecting a drug to be applied to the biological system based on the model.

6. The method of claim 1, further comprising:
    determining a predicted response time of the biological system, based on the model.

* * * * *